United States Patent
Moser et al.

(10) Patent No.: US 12,023,390 B2
(45) Date of Patent: Jul. 2, 2024

(54) ISOMERICALLY PURE $^{18}$F-LABELLED TETRAHYDROFOLATES

(71) Applicant: MERCK PATENT GMBH, Darmstadt (DE)

(72) Inventors: Rudolf Moser, Schaffhausen (CH); Viola Groehn, Dachsen (CH); Cristina Mueller, Nussbaumen (CH); Roger Schibli, Baden (CH); Simon Ametamey, Zurich (CH); Silvan Boss, Port (CH)

(73) Assignee: Merck Patent GmbH, Darmstadt (DE)

( * ) Notice: Subject to any disclaimer, the term of this patent is extended or adjusted under 35 U.S.C. 154(b) by 220 days.

(21) Appl. No.: 16/496,156

(22) PCT Filed: Mar. 19, 2018

(86) PCT No.: PCT/EP2018/056806
§ 371 (c)(1),
(2) Date: Sep. 20, 2019

(87) PCT Pub. No.: WO2018/172243
PCT Pub. Date: Sep. 27, 2018

(65) Prior Publication Data
US 2020/0306390 A1    Oct. 1, 2020

(30) Foreign Application Priority Data

Mar. 20, 2017    (EP) ..................... 17161884

(51) Int. Cl.
*A61K 51/04*    (2006.01)
*A61K 45/06*    (2006.01)

(52) U.S. Cl.
CPC .......... *A61K 51/0459* (2013.01); *A61K 45/06* (2013.01)

(58) Field of Classification Search
CPC .............................. A61K 51/0459; A61K 45/06

USPC ....................................................... 424/9.1
See application file for complete search history.

(56) References Cited

U.S. PATENT DOCUMENTS

| 9,771,368 B2 | 9/2017 | Ametamey et al. |
| 2013/0034496 A1* | 2/2013 | Kohen ................ C07D 475/12 424/1.81 |

FOREIGN PATENT DOCUMENTS

| WO | 08125617 A2 | 10/2008 | |
| WO | WO-2009103333 A1 * | 8/2009 | .......... C07D 475/04 |
| WO | 13167653 A1 | 11/2013 | |
| WO | WO-2013167653 A1 * | 11/2013 | ......... A61K 51/0459 |

OTHER PUBLICATIONS

Betzel et al.: "Radiosynthesis and Preclinical Evaluation of 3'-Aza-2'-[18F]fluorofblic Acid: A Novel PET Radiotracer for Folate Receptor Targeting", Bioconjug. Chem., vol. 24, 2013, pp. 205-214, XP055468030.
International Search Report PCT/EP2018/056806 dated Jun. 12, 2018 (pp. 1-2).
Soroka et al., "Absorption of iodofolic acids by the cells of malignant tumors", Russ J Bioorg Chem 2012, 38, 652-661 (Abst).
Search report and Opinion in corresponding Singapore application 11201908679Q dated Sep. 28, 2020 (pp. 1-2) and (pp. 1-6).

* cited by examiner

*Primary Examiner* — Michael G. Hartley
*Assistant Examiner* — Sean R Donohue
(74) *Attorney, Agent, or Firm* — MILLEN, WHITE, ZELANO AND BRANIGAN, P.C.; Harry B. Shubin

(57) ABSTRACT

The present invention is directed towards isomerically pure $^{18}$F-labelled (6S)- or (6R)-5-methyltetrahydrofolate radiopharmaceuticals, wherein the phenyl group within the folate structure, has been replaced by an $^{18}$F-labelled N-heterocycle, for use in diagnostic imaging of a cell or population of cells expressing a folate-receptor in vitro or in vivo or for use in monitoring of cancer or inflammatory and autoimmune diseases and therapy thereof.

15 Claims, 16 Drawing Sheets

ISOMERICALLY PURE $^{18}$F-LABELLED TETRAHYDROFOLATES

FIELD OF THE INVENTION

The present invention is directed towards the use of isomerically pure $^{18}$F-labelled (6S)- or (6R)-tetrahydrofolate radiopharmaceuticals, wherein the phenyl group within the folate structure, has been replaced by an $^{18}$F-labelled N-heterocycle, in diagnosis of a cell or population of cells expressing a folate-receptor and monitoring of cancer or inflammatory and autoimmune diseases and therapy thereof.

TECHNICAL BACKGROUND

Receptor-specific targeting for delivery of effector moieties such as diagnostic or therapeutic agents is a widely researched field and has led to the development of non-invasive diagnostic and/or therapeutic medical applications. In particular in the field of nuclear medicine procedures and treatments, which employ radioactive materials emitting electromagnetic radiations such as γ-rays or particle emitting radiation, selective localization of these radioactive materials in targeted cells or tissues is required to achieve either high signal intensity for visualization of specific tissues, assessing a disease and/or monitoring effects of therapeutic treatments, or high radiation dose, for delivering adequate doses of ionizing radiation to a specified diseased site, without the risk of radiation injury/radiotoxicity in other e.g. healthy tissues. It is thus of crucial interest to determine and assess cell-specific structures and in particular structures that are present in case of cancer (i.e. tumors) or inflammatory and autoimmune diseases, such as receptors, antigens, haptens and the like which can be specifically targeted by the respective biological vehicles.

In the past two decades, a large number of folic acid-based radiopharmaceuticals have been investigated for their ability to image folate receptor (FR) positive tumor tissues (Low, P. S., Henne, W., and Doorneweerd, D. (2008) Discovery and development of folic-acid-based receptor targeting for imaging and therapy of cancer and inflammatory diseases. *Acc. Chem. Res.* 41, 120-129; Philip Stewart Low, S. A. K. (2009) Folate-targeted therapeutic and imaging agents for cancer. *Curr. Opin. Chem. Biol.* 13, 256-262; Müller, C. (2013) Folate-Based Radiotracers for PET Imaging—Update and Perspectives. *Molecules* 18, 5005-5031, and Müller, Folate based radiopharmaceuticals for imaging and therapy of cancer and inflammation., C. Curr Pharm Des. 2012; 18(8): 1058-83). The FR-α represents an optimal target for tumor imaging since it is overexpressed on various epithelial cancer types such as ovarian, uterus, kidney, breast, lung and colon-rectum cancer, but only limited expression in healthy tissues including the kidney, choroid plexus, salivary glands, lung and placenta (Parker, N., Turk, M. J., Westrick, E., Lewis, J. D., Low, P. S., and Leamon, C. P. (2005) Folate receptor expression in carcinomas and normal tissues determined by a quantitative radioligand binding assay. *Anal. Biochem.* 338, 284-293.) Folic acid-based radiotracers have a drawback that they accumulate in the kidneys and other FR-positive tissues to a large extent due to their high binding affinity to FR-α (IC$_{50}$=~1 nM) (Müller, C. (2013) Folate-Based Radiotracers for PET Imaging—Update and Perspectives. *Molecules* 18, 5005-5031.) Furthermore, these folic-acid based radiotracers also bind the FR-β isoform, which is upregulated on activated macrophages involved in inflammation, with similar high affinity (Nakashima-Matsushita, N., Homma, T., Yu, S., Matsuda, T., Sunahara, N., Nakamura, T., Tsukano, M., Ratnam, M., and Matsuyama, T. (1999) Selective expression of folate receptor β and its possible role in methotrexate transport in synovial macrophages from patients with rheumatoid arthritis. *Arthritis Rheum.* 42, 1609-1616; Paulos, C. M., Turk, M. J., Breur, G. J., and Low, P. S. (2004) Folate receptor-mediated targeting of therapeutic and imaging agents to activated macrophages in rheumatoid arthritis. *Adv. Drug Deliv. Rev.* 56, 1205-1217.) This non-selectivity may result in false-positive outcomes of cancer diagnosis or follow-up studies. Therefore, a selective folate-based radiopharmaceutical would be of high importance and interest in order to reduce or even avoid misleading outcomes.

However so far, only a limited number of reduced folates have been radiolabeled for imaging studies. Vaitilingam et al. reported on 5,10-dimethyltetrahydrofolate derivative (DMTHF) which was labeled with $^{99m}$Tc, however, no information was provided about the diastereomeric ratio of the DMTHF derivative (Vaitilingam, B., Chelvam, V., Kularatne, S. a., Poh, S., Ayala-Lopez, W., and Low, P. S. (2012) A Folate Receptor-α-Specific Ligand That Targets Cancer Tissue and Not Sites of Inflammation. *J. Nucl. Med.* 53, 1127-1134.) The authors reported a K$_D$ value of 38 nM, which was four-fold higher compared to the corresponding oxidized form (EC20, K$_D$=12 nM). Selectivity for FR-α over FR-β was demonstrated in in vitro and in vivo experiments using FR-α-positive tumor and an animal model of inflammation. Besides the DMTHF derivative, Saeed et al. reported in Nuclear Medicine and Biology 39(5):697-71 January 2012 on another reduced folate radiotracer labeled with carbon-11, however, no results of in vitro or in vivo experiments have been published. Similar to Vaitlingam and colleagues, no information on the diastereomeric ratio of the radiolabeled product was provided. A fluorine-18 labeled folate PET tracer that selectively targets tumor-associated FR-α and not FR-β at inflammatory sites containing FR-β would be of high interest for providing significant sensitivity and specificity.

Wang et al reported in Biochemical Pharmacology. Vol. 44. No. 9. pp. 1898-1901, 1992 a 4-fold difference in binding affinities of the reduced 5-methyl-(6R)- resp. -(6S)-THF.

Betzel et al recently reported a promising fluorine-18 labeled folic acid derivative designated 3'-aza-2'-[$^{18}$F]fluorofolic acid for imaging FR-positive cancer tissue (Betzel, T., Müller, C., Groehn, V., Müller, A., Reber, J., Fischer, C. R., Kramer, S. D., Schibli, R., and Ametamey, S. M. (2013) Radiosynthesis and Preclinical Evaluation of 3'-Aza-2'-[$^{18}$F] fluorofolic Acid: A Novel PET Radiotracer for Folate Receptor Targeting. *Bioconjug. Chem.* 24, 205-214.)

Yet, while known $^{18}$F folate radiopharmaceuticals show promising results, there is still a need for compounds that show high FR-alpha-specificity and are suitable for routine clinical applications and yet can be obtained in efficient and versatile ways with high radiochemical yields.

Applicants have now found that high specificity for FR-alpha-positive tissue can be achieved with isomerically pure $^{18}$F-labelled tetrahydrofolate derivatives such as the physiological (6R)-form of 3'-aza-2'-[$^{18}$F]fluoro-5-methyltetrahydrofolate.

Isomerically pure $^{18}$F-labelled tetrahydrofolate derivatives such as 3'-aza-2'-[$^{18}$F]fluoro-5-methyltetrahydrofolate, which is a derivative of the reduced physiological folate form binds to the FR with high affinity and exhibits a 50-fold higher selectivity for FR-alpha than the respective oxidized folic acid derivative. A PET tracer that selectively targets tumor associated FR-alpha and not FR-beta at inflammatory sites containing FR-beta is providing significant sensitivity and specificity. Having deduced from picture of an unspecific PET tracer what is coming from a PET tracer that selectively targets tumor associated FR-alpha one can gain information on inflammatory sites containing FR-beta.

Thus, the present invention is directed to the use of isomerically pure $^{18}$F-labelled tetrahydrofolate radiopharmaceuticals in diagnostic imaging of a cell or population of cells expressing a folate-receptor in vitro or in vivo or for the use in monitoring of cancer or inflammatory and autoimmune diseases and therapy thereof.

SUMMARY OF THE INVENTION

The present invention is directed in a first aspect to the use of isomerically pure $^{18}$F-labelled tetrahydrofolate radiopharmaceuticals, wherein the phenyl group within the folate structure, has been replaced by an $^{18}$F-labelled N-heterocycle in diagnostic imaging of a cell or population of cells expressing a folate-receptor in vitro or in vivo or for use in monitoring of cancer or inflammatory and autoimmune diseases and therapy thereof.

Preferably, the $^{18}$F-labelled tetrahydrofolate radiopharmaceuticals, wherein the phenyl group within the folate structure, has been replaced by an $^{18}$F-labelled N-heterocycle are in their isomerically pure (6S)- or (6R)-form.

Even more preferably, the isomerically pure $^{18}$F-labelled (6S)- or (6R)-tetrahydrofolate radiopharmaceuticals, wherein the phenyl group within the folate structure, has been replaced by an $^{18}$F-labelled N-heterocycle is an isomerically pure $^{18}$F-labelled 5-methyl-(6S)-tetrahydrofolate or an isomerically pure $^{18}$F-labelled 5-methyl-(6R)-tetrahydrofolate radiopharmaceuticals, wherein the phenyl group within the folate structure, has been replaced by an $^{18}$F-labelled N-heterocycle.

In specific embodiments the isomerically pure $^{18}$F-labelled (6S)- or (6R)-tetrahydrofolate radiopharmaceutical, wherein the phenyl group within the folate structure, has been replaced by an $^{18}$F-labelled N-heterocycle is an isomerically pure 3'-aza-2'-[$^{18}$F]fluoro-5-methyl-(6S)-tetrahydrofolate or an isomerically pure 3'-aza-2'-[$^{18}$F]fluoro-5-methyl-(6R)-tetrahydrofolate.

In one specific embodiment, there is provided a compound of formula Ia or Ib for use in diagnostic imaging of a cell or population of cells expressing a folate-receptor in vitro or in vivo or for use in monitoring of cancer or inflammatory and autoimmune diseases and therapy thereof

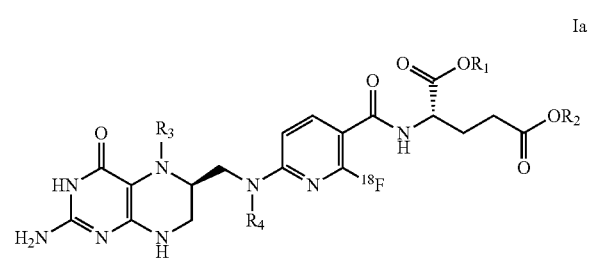

Ia

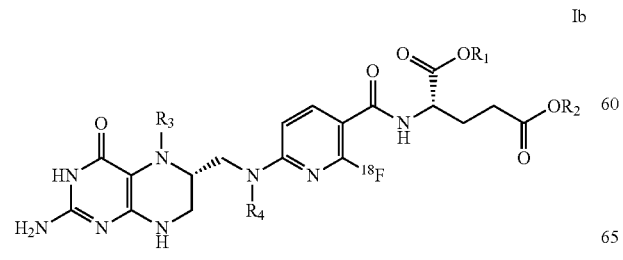

Ib wherein $R_1$, $R_2$ are independently of each other H or straight chain or branched C1-C6 alkyl, and $R_3$, $R_4$ are independently of each other H, formyl, or methyl, or a pharmaceutically acceptable salt thereof.

In a preferred embodiment, $R_1$, $R_2$ are independently of each other H or straight chain or branched C1-C6 alkyl, and $R_3$ is methyl, and $R_4$ is H, or a pharmaceutically acceptable salt thereof.

More specifically the present invention is directed towards a compound having formulas IIa or IIb for use in diagnostic imaging of a cell or population of cells expressing a folate-receptor in vitro or in vivo or for use in monitoring of cancer or inflammatory and autoimmune diseases and therapy thereof

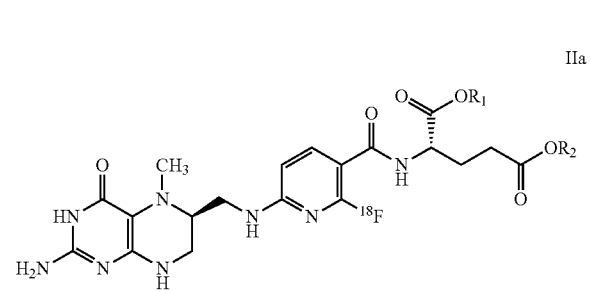

IIa

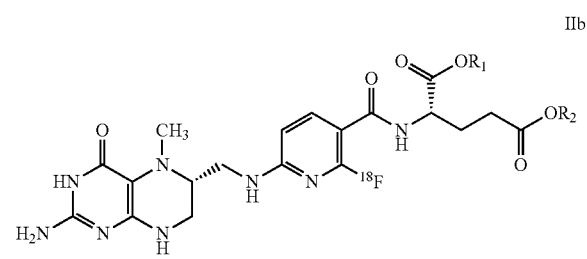

IIb wherein $R_1$, $R_2$ are independently of each other H, or C1-C12 alkyl, or a pharmaceutically acceptable salt thereof.

In a preferred embodiment, the present invention is directed towards a compound having formulas IIIa or IIIb for use in diagnostic imaging of a cell or population of cells expressing a folate-receptor in vitro or in vivo or for use in monitoring of cancer or inflammatory and autoimmune diseases and therapy thereof

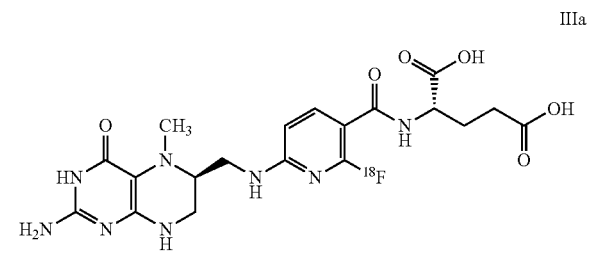

IIIa

IIIb

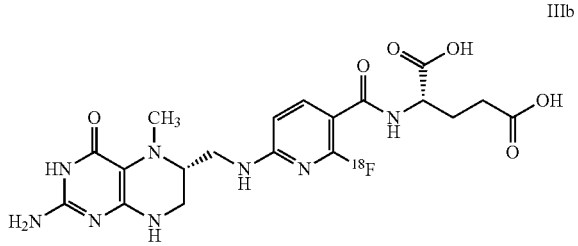

or a pharmaceutically acceptable salt thereof.

In specific embodiments the isomerically pure $^{18}$F-labelled (6S)- or (6R)-tetrahydrofolate radiopharmaceutical, wherein the phenyl group within the folate structure, has been replaced by an $^{18}$F-labelled N-heterocycle is directed to alkali or alkaline earth metal salts, preferably sodium, potassium, magnesium or calcium salts.

In a further aspect, the present invention is directed to the use of isomerically pure $^{18}$F-labelled (6S)- or (6R)-tetrahydrofolate radiopharmaceuticals, wherein the phenyl group within the folate structure, has been replaced by an $^{18}$F-labelled N-heterocycle (or pharmaceutical compositions thereof) in diagnosis or therapy, preferably of cancer or inflammatory and autoimmune diseases.

In specific embodiments the present invention is directed to the use of isomerically pure $^{18}$F-labelled (6S)- or (6R)-tetrahydrofolate radiopharmaceuticals, wherein the phenyl group within the folate structure, has been replaced by an $^{18}$F-labelled N-heterocycle (or pharmaceutical compositions thereof) in monitoring cancer or inflammatory and autoimmune disease therapy in a subject comprising the steps of (i) administering to a subject in need isomerically pure $^{18}$F-labelled (6S)- or (6R)-tetrahydrofolate radiopharmaceuticals, wherein the phenyl group within the folate structure, has been replaced by an $^{18}$F-labelled N-heterocycle in a diagnostic imaging amount in combination with a therapeutically active, and (ii) performing diagnostic imaging using PET by detecting a signal from said at least one compound to follow the course of cancer or inflammatory and autoimmune disease therapy.

In an even further aspect, the present invention is directed to the use of isomerically pure $^{18}$F-labelled (6S)- or (6R)-tetrahydrofolate radiopharmaceuticals, wherein the phenyl group within the folate structure, has been replaced by an $^{18}$F-labelled N-heterocycle (or pharmaceutical compositions thereof) in diagnostic imaging of a cell or population of cells expressing a folate-receptor.

DETAILED DESCRIPTION

Figure 1:
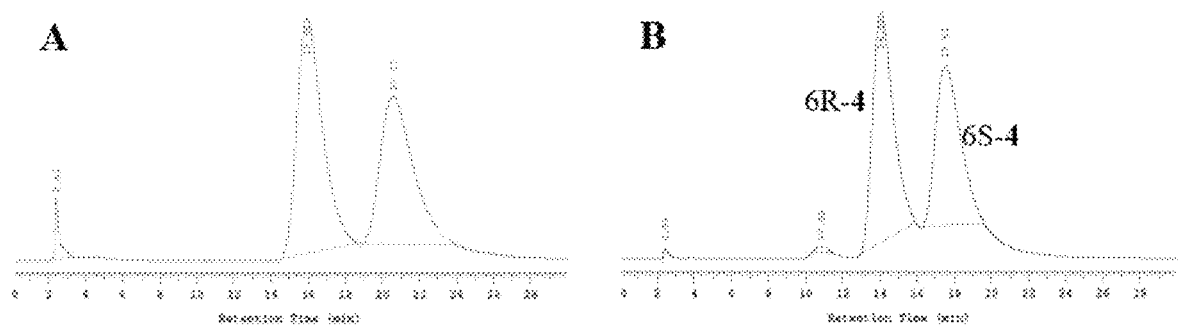
FIG. 1: Chiral HPLC chromatograms of the precursor N$^2$-acetyl-3'-aza-2'-chloro-5-methyltetrahydrofolate-di-tert-butylester 6S-2 and 6R-2 (A) and the protected reference N$^2$-acetyl-3'-aza-2'-fluoro-5-methyltetrahydrofolate-di-tert-butylester 6S-2 and 6R-2 (B).

The present invention is directed in a first aspect to the use of isomerically pure ${}^{18}$F-labelled tetrahydrofolate radiopharmaceuticals, wherein the phenyl group within the folate structure, has been replaced by an ${}^{18}$F-labelled N-heterocycle in diagnostic imaging of a cell or population of cells expressing a folate-receptor in vitro or in vivo or for use in monitoring of cancer or inflammatory and autoimmune diseases and therapy thereof.

The term "tetrahydrofolate" or "tetrahydrofolates" as used herein, comprises compounds based on the structure of 5,6,7,8-tetrahydrofolic acid. Tetrahydrofolates (abbreviated THF) as 5-methyl-THF distinguish themselves from their oxidized form, such as folic acid, by the additional chiral centre at C6, which leads to the isomeric (6S)- and (6R)-forms. The α-carbon of the glutamic acid moiety is in both the folic acid and the tetrahydrofolates as defined herein in the naturally occurring configuration. The compounds for use according to the present invention are preferably in a isomerically pure form.

Tetrahydrofolates as used herein comprise the acid form of the tetrahydrofolate and also the respective ester forms.

The terms "isomerically pure" resp. "stereoisomerically pure", as used herein, mean the compound of the invention having an isomeric excess of the one form against the other one [(6R)-form to the (6S)-form or (6S)-form to the (6R)-form] of greater than about 80%, preferably greater than about 90%, preferably greater than about 95%, more preferably greater than about 97%, even more preferably greater than about 99% or more, and most preferably up to 100%, wherein the remainder may be one or more of the other isomers.

In one specific embodiment, there is provided a ${}^{18}$F-labelled tetrahydrofolate radiopharmaceuticals of general formula Ia or Ib or a pharmaceutically acceptable salt thereof for use in diagnostic imaging of a cell or population of cells expressing a folate-receptor in vitro or in vivo or for use in monitoring of cancer or inflammatory and autoimmune diseases and therapy thereof

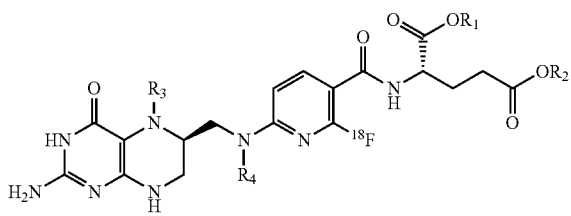

Ia

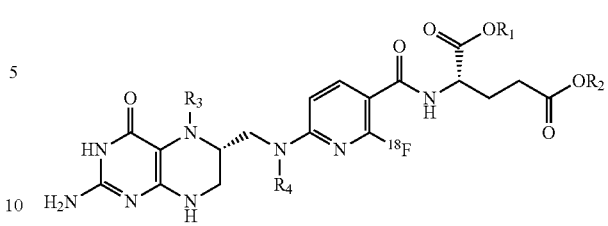

Ib

Wherein $R_1$, $R_2$ are independently of each other H or straight chain or branched C1-C6 alkyl, and $R_3$, $R_4$ are independently of each other H, formyl, or methyl.

The term "alkyl", when used singly or in combination, refers to straight chain or branched alkyl groups containing in the indicted number of C-atoms, typically containing 1 to 6, preferably 1 to 4 carbon atoms, such as methyl, ethyl, propyl, isopropyl, butyl, sec-butyl, isobutyl, t-butyl and the like.

Pharmaceutically acceptable salts can be alkali or alkaline earth metal salts, preferably sodium, potassium, magnesium or calcium salts or can also be acidic salts, such as sulfate or sulfonate salts, preferably sulfate salts.

Thus, in specific embodiments, the present invention is directed towards compounds of formula IIa or IIb or a pharmaceutically acceptable salt thereof for use in diagnostic imaging of a cell or population of cells expressing a folate-receptor in vitro or in vivo or for use in monitoring of cancer or inflammatory and autoimmune diseases and therapy thereof,

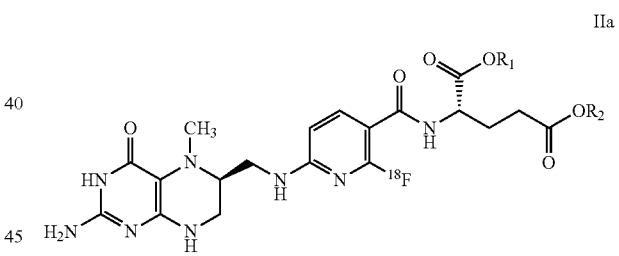

IIa

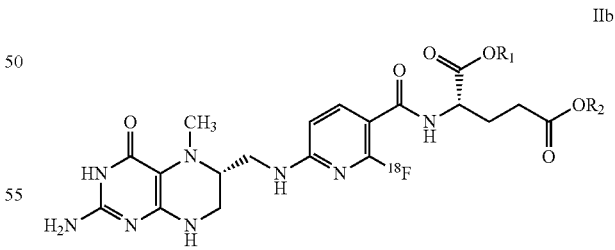

IIb wherein $R_1$, $R_2$ are independently of each other H, or C1-C12 alkyl.

Even more specifically the present invention is directed towards a compound formulas Ma or Mb or a pharmaceutically acceptable salt thereof for use in diagnostic imaging of a cell or population of cells expressing a folate-receptor in vitro or in vivo or for use in monitoring of cancer or inflammatory and autoimmune diseases and therapy thereof

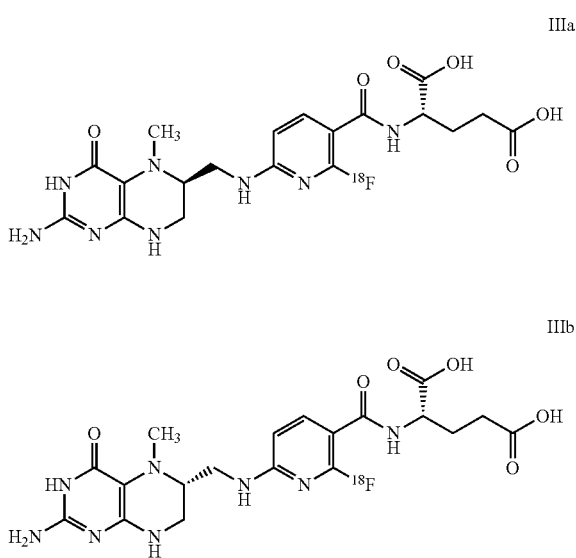

IIIa

IIIb

It was found that the isomerically pure $^{18}$F-labelled tetrahydrofolate radiopharmaceuticals, wherein the phenyl group within the folate structure, has been replaced by an $^{18}$F-labelled N-heterocycle surprisingly show comparable binding affinities to the FR.

Even more surprisingly it was found that the isomerically pure $^{18}$F-labelled tetrahydrofolate radiopharmaceuticals, wherein the phenyl group within the folate structure, has been replaced by an $^{18}$F-labelled N-heterocycle show a different biodistribution. This is highly surprising as in vitro data did show a similar FR-affinity for both isomers.

Isomerically pure $^{18}$F-labelled tetrahydrofolate radiopharmaceuticals, wherein the phenyl group within the folate structure, has been replaced by an $^{18}$F-labelled N-heterocycle outperformed the corresponding oxidized folic acid-based derivative in terms of tumor uptake, biodistribution and in vivo stability.

Overall isomerically pure $^{18}$F-labelled tetrahydrofolate radiopharmaceuticals, wherein the phenyl group within the folate structure, has been replaced by an $^{18}$F-labelled N-heterocycle accumulate very specifically in FR positive tissue. Such accumulation could not be expected as $^{18}$F-labelled tetrahydrofolate radiopharmaceuticals in fact are transported via carrier systems into the tissue. Especially the (6S)-form does show in this regard a behaviour as the oxidized form does.

The disclosed remarkably improved tumor to kidney ratio, especially for the (6R)-form of $^{18}$F-labelled tetrahydrofolate radiopharmaceuticals, wherein the phenyl group within the folate structure, has been replaced by an $^{18}$F-labelled N-heterocycle, is highly surprising and could not be expected.

In a further aspect the present invention is directed towards a method for diagnostic imaging of a cell or population of cells expressing a folate-receptor, said method comprising the steps of administering at least one compound according to formula Ia, Ib, IIa, IIb, IIIa, or IIIb in a diagnostic imaging amount, and obtaining a diagnostic image of said cell or population of cells.

In yet a further aspect the present invention provides uses of isomerically pure $^{18}$F-labelled tetrahydrofolate radiopharmaceuticals for convenient and effective administration to a subject in need for diagnostic imaging.

Thus the present invention provides a method for diagnostic imaging of a cell or population of cells expressing a folate-receptor, said method comprising the steps of administering at least one isomerically pure $^{18}$F-labelled tetrahydrofolate radiopharmaceutical of the invention in a diagnostic imaging amount, and obtaining a diagnostic image of said cell or population of cells.

Such imaging may be performed on a cell or population of cells expressing a folate-receptor in vitro or ex vivo (biopsies) or in vivo. Typical cells or population of cells overexpressing the folate receptor-α are epithelial cancer types such as ovarian, uterus, kidney, breast, lung and colon-rectum cancer.

Thus, the present invention provides a method for in vitro detection of a cell expressing the folate receptor in a tissue sample which includes contacting said tissue sample with at least one isomerically pure $^{18}$F-labelled tetrahydrofolate radiopharmaceutical of the invention in effective amounts and for sufficient time and conditions to al-low binding to occur and detecting such binding by PET imaging.

In a further aspect the present invention provides uses of isomerically pure $^{18}$F-labelled tetrahydrofolate radiopharmaceuticals of the present invention for convenient and effective administration to a subject in need for diagnostic imaging or monitoring of cancer therapy or therapy of inflammatory and autoimmune diseases.

In another aspect the present invention provides a method for simultaneous diagnosis and therapy, comprising the steps of administering to a subject in need thereof at least one isomerically pure $^{18}$F-labelled tetrahydrofolate radiopharmaceutical of the present invention in a diagnostically effective amount in combination with a therapeutically active, and obtaining a diagnostic image of said tissues to follow the course of treatment.

The subject of the methods of the present invention is preferably a mammal, such as an animal or a human, preferably a human.

The dosage depends on the nature of the effect desired, such as the form of diagnosis or therapy, on the kind and frequency of treatment, on the diagnostic instrumentation, on the form of application of the preparation, and on the age, weight, nutrition and condition of the recipient, kind of concurrent treatment, if any.

However, the most preferred dosage can be tailored to the individual subject, as is understood and determinable by one of skill in the art, without undue experimentation. This typically involves adjustment of a standard dose, e.g., reduction of the dose if the patient has a low body weight.

Treatment can commence with a smaller amount, below the optimum amount, which can be increased in order to achieve the optimum effect. The imaging procedure in the PET scanner takes place from within minutes to 2-4 hours after administration of the radiotracer. The schedule depends on the imaging target and kinetics of the radiotracer as well as the desired information.

The preferred route of administration of the isomerically pure $^{18}$F-labelled tetrahydrofolate radiopharmaceuticals of the present invention is by parenterally e.g. by intravenous injection. The suitable forms for injection include sterile aqueous solutions or dispersions of the above mentioned isomerically pure $^{18}$F-labelled tetrahydrofolate radiopharmaceuticals of the present invention. Typically the radiopharmaceutical will be formulated in physiological buffer solutions.

Isomerically pure $^{18}$F-labelled tetrahydrofolate radiopharmaceuticals undergo sterilization by any art recognized technique, including but not limited to, addition of antibacterial of antifungal agents, for example, paraben, chlorobutanol, phenol, sorbic acid, thimerosal, and the like. Preferably they undergo a sterile filtration before administration eliminating the need of additional sterilisation agents.

For a solution to be injected a preferred unit dosage is from about 0.01 ml to about 10 ml. After parenteral administration, imaging of the organ or tumor in vivo can take place, if desired, from within minutes to 2 to 4 hours after the radiolabeled reagent has been administered to a subject to allow a sufficient amount of the administered dose to accumulate in the targeted area of choice.

Isomerically pure $^{18}$F-labelled tetrahydrofolate radiopharmaceuticals of the invention may also be used for in vitro detection of a cell expressing the folate receptor in a tissue biopsy taken from a subject. Thus in a further embodiment the present invention provides a method for in vitro detection of a cell expressing the folate receptor, e.g. a tumor cell, in a tissue sample which includes contacting said tissue sample with isomerically pure $^{18}$F-labelled tetrahydrofolate radiopharmaceuticals of the present invention in effective amounts and for sufficient time and conditions to allow binding to occur and detecting such binding by imaging techniques.

Samples can be collected by procedures known to the skilled person, e.g., by collecting a tissue biopsy or a body fluid, by aspirating for tracheal or pulmonary samples and the like.

Tissue samples to be tested include any tissue suspected to contain a cell expressing a folate receptor, such as tumor cells, epithelial cells, kidneys, gastrointestinal or the hepatobiliary system, and others. Samples can be sectioned, e.g., with a microtome, to facilitate microscopic examination and observation. Samples can also be fixed with an appropriate fixative either before or after incubation with one of the $^{18}$F-labelled tetrahydrofolate radiopharmaceuticals of the present invention to improve the histological quality of sample tissues.

Time and conditions sufficient for binding of isomerically pure $^{18}$F-labelled tetrahydrofolate radiopharmaceuticals of the present invention to a folate receptor on the cell include standard tissue culture conditions, i.e. samples can be cultured in vitro and incubated with one of the complexes or compositions of the present invention in physiological media. Such conditions are well known to the skilled person. Alternatively, samples can be fixed and then incubated with isomerically pure $^{18}$F-labelled tetrahydrofolate radiopharmaceuticals of the present invention in an isotonic or physiological buffer.

For all applications it is convenient to prepare isomerically pure $^{18}$F-labelled tetrahydrofolate radiopharmaceuticals of the present invention at, or near, the site where they are to be used.

All of the compounds and/or methods disclosed and claimed herein can be made and executed without undue experimentation in light of the present disclosure. It will be apparent to those of skill in the art that variations may be applied to the present invention without departing from the scope of the invention. The Examples provided herein are intended to be illustrative and are not exhaustive; therefore the illustrated Examples should not be viewed as limiting the invention in any way.

EXAMPLES

Materials and Methods
General:

Reagents and solvents were purchased from Sigma-Aldrich Chemie GmbH, Acros Organis and used without purification. The building blocks were bought from ABCR-Chemicals, Apollo Scientific, Fluka-Chemie and Merck & Cie (Schaffhausen, Switzerland). 6R-10-formyl-5-methyl-tetrahydropteroic acid (6R-10-formyl-5-MTHP) was provided by Merck & Cie (Schaffhausen, Switzerland). Quality control of these building blocks was performed with $^1$H-NMR, $^{13}$C-NMR, cosygp and HR-MS.

The solvents for conducting the flash chromatography, transferring reaction mixtures, extraction and washing processes were directly purchased from the fuel depot from ETH.

Analytical Methods:

Nuclear magnetic resonance spectra were recorded on a Bruker 400 or 500 MHz spectrometer with the corresponding solvent signals as an internal standard. Chemical shifts are reported in parts per million (ppm) relative to tetramethylsilane (0.00 ppm). Values of the coupling constant (J) are given in hertz (Hz); the following abbreviations are used in this section for the description of the $^1$H NMR: singlet (s), doublet (d), triplet (t), quartet (q), multiplet (m), doublet of doublets (dd), doublet of doublets of doublets (ddd) and broad signal (bs). The chemical shifts of complex multiplets are given as the range of their occurrence.

High-resolution mass spectra (HR-MS) were recorded by the MS service of the Laboratorium filr Organische Chemie at ETH Zurich on a Varian IonSpec Ultima MALDI-FT-ICR or a Bruker Daltonics Ultra-Flex II MALDI-TOF. Trans-243-(4-tert-Butylphenyl)-2-methyl-2-propenyli-denelmalononitrile (DCTB) and 3-hydroxypyridine-2-carboxylic acid (3-HPA) served as matrices for MALDI mass spectrometry. ESI mass spectra were recorded with a Bruker FTMS 4.7 T BioAPEXII (ESI).

Preparative HPLC was performed with a Merck-Hitachi system, equipped with a D7000 interface, L-7400 UV detector, and a L-7150 pump, using an Ultimate XB-C18 column (150×21.2 mm, 5 μm) (Ultisil, Welch Materials) at a flow rate of 15 mL/min (280 nm).

Analytical HPLC was performed with a Merck-Hitachi system, equipped with a D-7000 interface, L-7400 UV detector, and a L-7100 pump, using a sunfire C18 column (4.6×150 mm, 5 μm). If not described otherwise, reaction control was performed via analytical HPLC using 10 mM NH$_4$HCO$_3$ solution (solvent A) and MeCN (solvent B) and the following gradient: 0-30 min 100-60% A, 30-35 min: 60% A, 35-36 min: 60-100% A, 36-40 min: 100% A at a flow rate of 1 mL/min and at 280 nm.

Semi-preparative HPLC was performed with a Merck-Hitachi system, equipped with a D-7000 interface, L-7400 UV detector, and a L-7100 pump, with a sunfire C18 column (10×150 mm, 5 μm) using 10 mM NH$_4$HCO$_3$ buffer (solvent A) and MeCN (solvent B) as solvent system at a flow rate of 4 mL/min at 280 nm.

Analytical radio-HPLC was performed on an Agilent 1100 series HPLC system, equipped with a 100 μL-lop and a GabiStar radiodetector (Raytest). The analytical Phenomenex Gemini C18 column (4.6×250 mm, 5 μm, 110 Å, no precolumn) was used at a flow rate 1 mL/min at 280 nm. Analytical HPLC was performed with 10 mM NH$_4$HCO$_3$ (solvent A) and MeCN (solvent B) as solvent system with the gradient as follows: 0-20 min: 95-60% A, 20-25 min 60% A, 25-26 min 60-95% A, 26-30 min: 95% A.

Reaction control was performed with a radio ultra-performance liquid chromatography (radio-UPLC, Waters) using an Acquity UPLC BEH C18 column (2.1×50 mm, 1.7 µm, Waters) and an attached coincidence detector (FlowStar LB513, Berthold) and with a 10 mM $NH_4HCO_3$ solution (solvent A), and MeCN (solvent B) as solvent system with the following gradient: 0-0.3 min 90% A, 0.3-3.0 min 90% 50% A, 3.0-3.1 min: 50-20% A, 3.1-3.5 min 20% A, 3.5-3.6 min 20-90% A, 3.6-4.0 min 90% A at a flow rate of 0.6 mL/min and at 280 nm.

Radiochemistry: Production of Dried [$^{18}$F]Fluoride:

No-carrier-added [$^{18}$F]fluoride was obtained by irradiation of a liquid target, filled with isotopically enriched [$^{18}$O]$H_2O$ (930 µL, 97%, Cambridge Isotope Laboratories) by an 18 MeV proton beam on a 18/9 cyclotron (IBA, Belgium). The radioactivity (36-45 GBq) was transferred to a synthesis hot cell by a continuous stream of helium. The aqueous [$^{18}$F]fluoride solution was trapped on a Sep-Pak Light Accell Plus carb QMA cartridge (Waters) without preconditioning. Elution was performed by using a solution of either $K_2CO_3$ (1.2 mg, 8.7 µmol) and Kryptofix (10 mg, 26.6 µmol) or $Cs_2CO_3$ (2.8 mg, 8.6 µmol) and Kryptofix (5 mg, 13.3 µmol) in a mixture of $H_2O$ (0.6 mL) and MeCN (1.4 mL). The eluate was collected in a sealed Wheaton reactor (5 mL) and the solvent was evaporated at 95° C. under reduced pressure and a gentle stream of nitrogen for 10 min Subsequently, MeCN (1 mL) was added three times and evaporated to dryness within 3 min at 95° C. Finally, full vacuum without nitrogen stream was applied for 5 min at 95° C.

Biodistriution Studies:

Biodistribution studies were performed 2 weeks after cell inoculation. The $^{18}$F-folate radiotracers (~5 MBq/mouse) were injected in a volume of 100 µL into a lateral tail vein. The animals were sacrificed at 30 min, 60 min and 90 min after administration of radiotracers. Selected tissues and organs were collected, weighed, and radioactivity was measured using a γ-counter. The results were listed as a percentage of the injected radioactivity per gram of tissue mass (% IA/g), using counts of a defined volume of the original injection solution measured at the same time resulting in decay corrected values.

PET/CT Imaging Studies:

Mice were prepared the same way as for biodistribution studies. A bench-top preclinical PET scanner (Genisys[8], Sofie Biosciences, U.S. and Perkin Elmer, U.S.) was employed for the PET/CT scans of the mice. The energy window was set to 150-650 keV. Mice were injected intravenously with the 18F-radiotracers (~5 MBq in 100 µL). During the scans, which lasted for 10 min, the mice were anesthetized using a mixture of isoflurane and oxygen. Scans were performed at 1 h, 2 h and 3 h after injection of the $^{18}$F-radiotracers using G8 acquisition software (version 2.0.0.10). The images were reconstructed with maximum-likelihood expectation maximization (MLEM). For presenting the PET/CT images, the scale of the images was adjusted allowing optimal visualization of the tumor tissue and kidneys. (Approx. 10% at the lower scale were cut).

Example 1: Synthesis and Separation (by Chiral HPLC) of 6S- and 6R-$N^2$-Acetyl-3'-Aza-2'-Fluoro/2'-Chloro-5-Methyltetrahydrofolate Di-Tert-Butylester

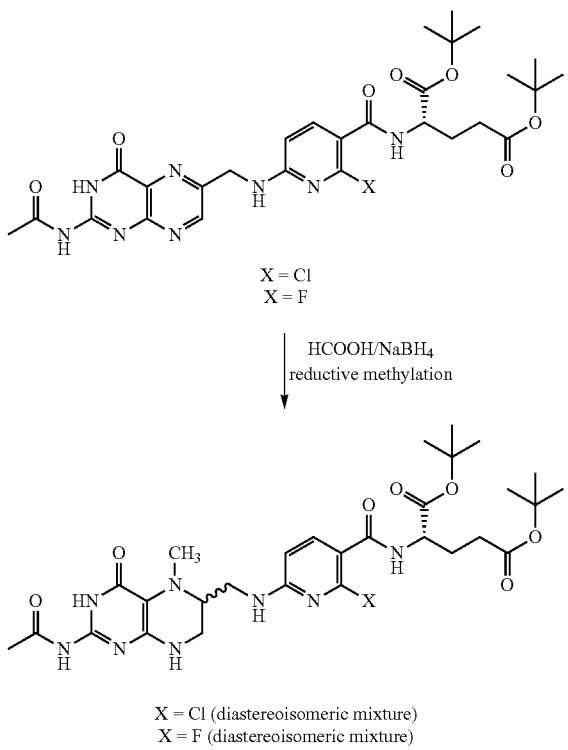

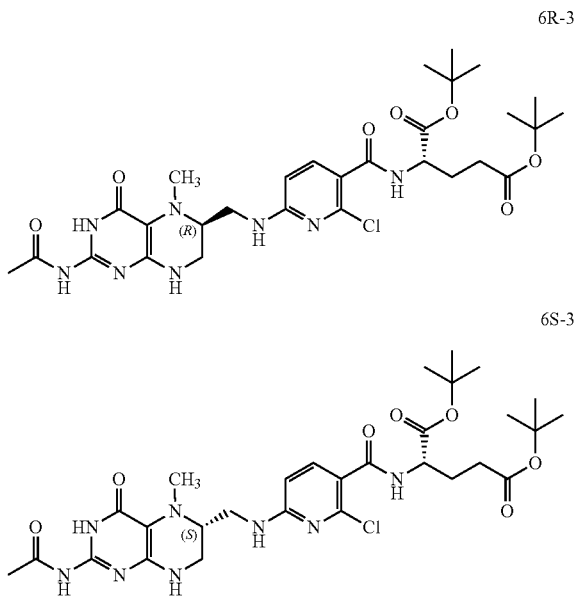

-continued 6R-2

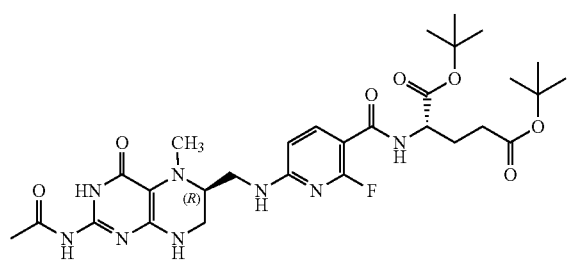

6S-2

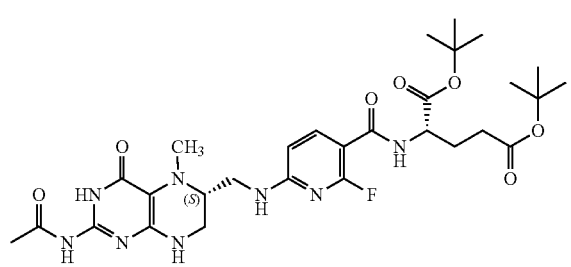

The synthesis of the 1:1 diastereomeric mixtures of 6S- and 6R-N²-acetyl-3'-aza-2'-chloro-5-MTHF-di-tert-butylester and 6S- and 6R-N²-acetyl-3'-aza-2'-fluoro-5-MTHF-di-tert-butylester were achieved by reductive methylation of N²-acetyl-3'-aza-2'-chloro-folic acid-di-tert-butylester and N²-acetyl-3'-aza-2'-fluoro-folic acid-di-tert-butylester (Scheme 1a) in analogy to a general method described in literature ("Reactions of Sodium Borohydride in Acidic Media. I. Reduction of Indoles and Alkylation of Aromatic Amines with Carboxylic Acids", G. W. Gribble, P. D. Lord, J. Skotnicki, S. E. Dietz, J. T. Eaton, J. L. Johnson, *J. Am. Chem. Soc.* 1974, 96, p. 7812) using methyl tert butyl ether and tetrahydrofurane as solvents. The products were characterized by LC-MS, ¹H-NMR and HPLC. The synthesis of N²-Acetyl-3'-aza-2'-chloro-folic acid-di-tert-butylester and N²—Acetyl-3'-aza-2'-fluoro-folic acid-di-tert-butylester was achieved according to WO 2013/167653. Chiral separation of the two diastereoisomers of both mixtures into the compounds as disclosed in Scheme 1b was achieved using the Reprosil 100 Chiral-NR HPLC column running on normal phase (isocratic, hexane/isopropanol 1:1, FIG. 1). 6R-N²-acetyl-3'-aza-2'-fluoro-5-methyltetrahydrofolate-di-tert-butylester (6R-2) refers to the diastereoisomer, which eluted first at 14.0 min, whereas 6S-N²-acetyl-3'-aza-2'-fluoro-5-methyltetrahydrofolate-di-tert-butylester (6S-2) refers to the isomer which eluted second at 17.5 min

Example 2: Synthesis of 6R-3'-Aza-2'-Fluoro-5-Methyltetrahydrofolate

Pure diastereomeric 6R-2 and 6S-2 were obtained after chiral separation (FIG. 1) and used as starting materials for the synthesis of 6R-1 and 6S-1. Acidic deprotection of 6R-2 and 6S-2 in acetone afforded after purification 6R- and 6-3'-aza-2'-fluoro-5-MTHF 6R-1 and 6S-1 in chemical yields of 81% and 87%, respectively (Scheme 1c).

Scheme 1c

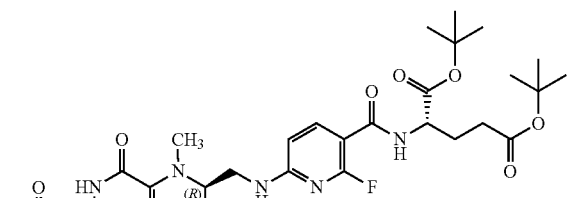

6R-2

↓ i

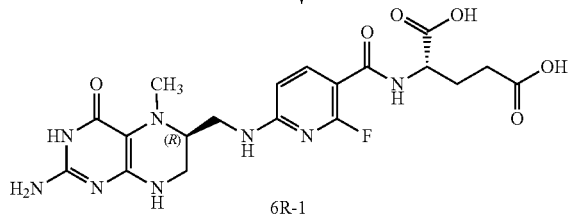

6R-1
87%

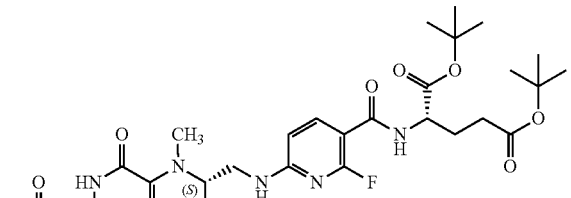

6S-2

↓ i

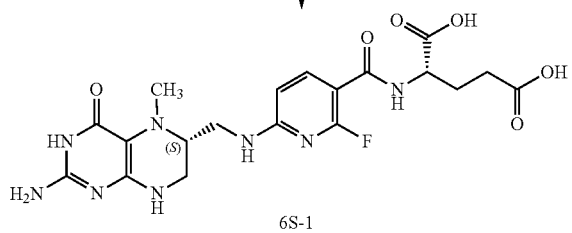

6S-1
81%

ª(i) 4M HCl, acetone, 70° C., 1 h.

6R-2 (7.00 mg, 11.1 μmoL) was dissolved in acetone (200 μL) and 4M HCl (500 μL) and stirred for 1 h at 70° C. (Scheme 1b). After completion of the reaction, the solution was neutralized with 4M NaOH and the product was purified by semipreparative HPLC. Lyophilisation of the product fractions afforded 6R-γ-1 as a white solid in 87% yield (4.62 mg) and high chemical and diastereomeric purity of >95%.

Example 3: Synthesis of 6S-3'-Aza-2'-Fluoro-5-Methyltetrahydrofolate 6S-2 (8.00 mg, 12.6 μmoL) was dissolved in acetone (200 μL) and 4M HCl (500 μL) and stirred for 1 h at 70° C. (Scheme 1b). After completion of the reaction, the solution was neutralized with 4M NaOH and the product was purified by semipreparative HPLC. Lyophilisation of the product fractions afforded 6S-γ-1 as a white solid in 81% yield (4.96 mg) and high chemical and diastereomeric purity of >95%.

Example 4: Determination of the Absolute Configuration of the Two Reference Diastereoisomers (6R-1 and 6S-1) by Circular Dichroism (CD)

Figure 2:
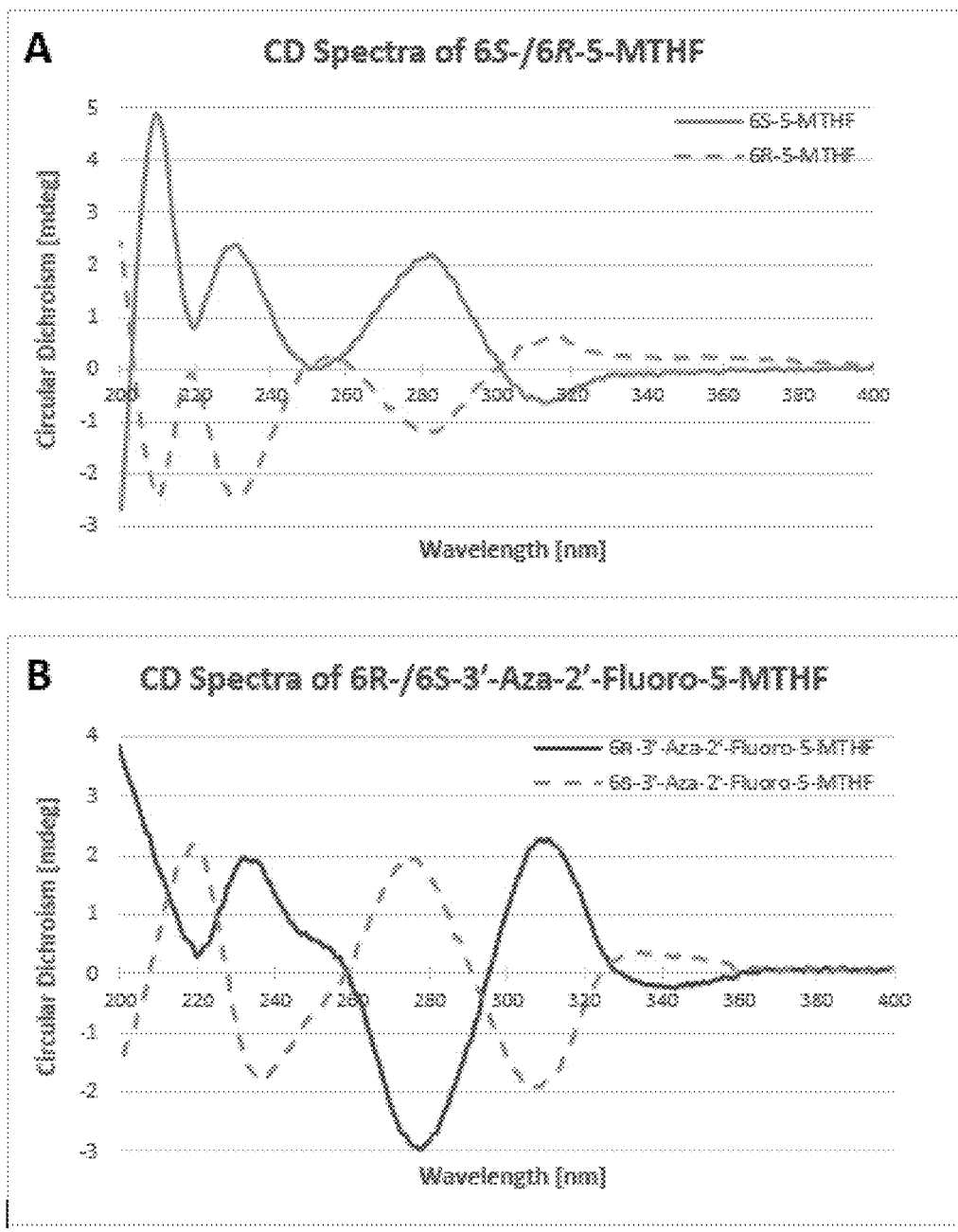
FIG. 2: CD spectra of 6S- and 6R-5-MTHF (A) and 6R-1 and 6S-1 (B) measuring from 400 nm to 200 nm.
Figure 3:
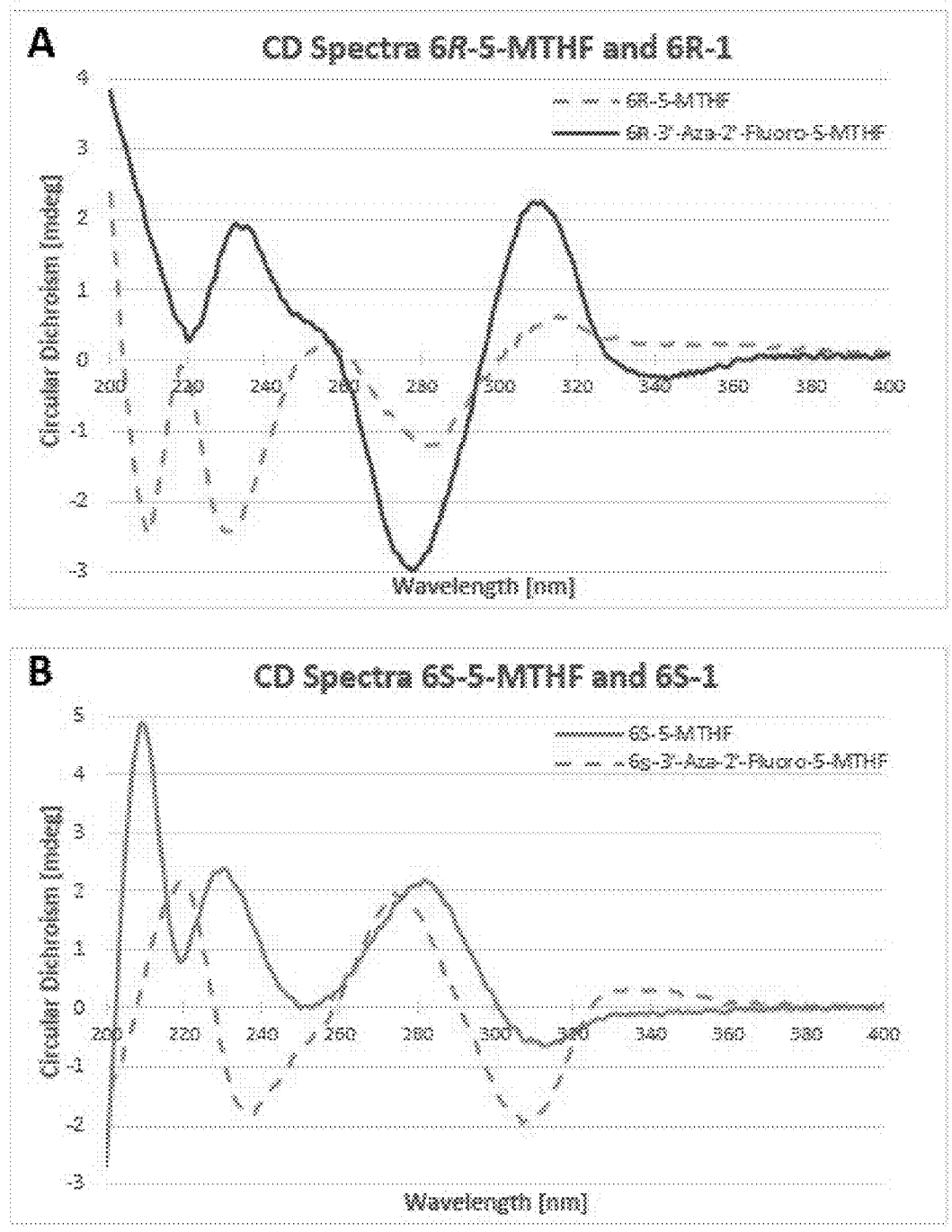
FIG. 3: Overlay of the CD spectra of 6S-5-MTHF and 6S-3'-aza-2'-fluoro-5-MTHF (A) and 6R-5-MTHF and 6R-3'-aza-2'-fluoro-5-MTHF (B).

CD spectra of 6S- and 6R-5-MTHF and the two reference compounds 6R- and 6S-3'-aza-2'-fluoro-5-MTHF (6R-1 and 6S-1) were recorded (FIGS. 2A and 2B). Opposite spectra were obtained for the two corresponding 6R- and 6S-diasteroisomers of each of the two pairs of folates. The spectra of the 6S- and 6R-5-MTHF served as reference spectra, since the stereochemistry of these two substances was known. It is reported in the literature that the pterin shows a typical absorption band at around 345 nm and a second band at 280 nm. These two typical absorption bands are also visible in all the four recorded CD spectra. Correlation of the reference spectra of 6S- and 6R-5-MTHF with the spectra of the two reference diastereoisomers 6R- and 6S-3'-aza-2'-fluoro-5-MTHFs could be done (FIG. 3). Since the peaks at 310 nm of 6R-5-MTHF and 6R-3'-Aza-2'-Fluoro-5-MTHF are both negative and the peaks at 280 nm are both positive, it can be assumed that the 6R-3'-Aza-2'-Fluoro-5-MTHF is the 6R-isomer (FIG. 3A), since these absorptions originate from the pterin bearing the stereocenter. The same correlation could be done with 6S-3'-aza-2'-fluoro-5-MTHF and 6S-5-MTHF (FIG. 3B), where the peaks at 310 nm are positive and the both peaks at 280 nm negative. Based on these results it can be concluded that the 6S-3'-aza-2'-fluoro-5-MTHF is S-configured at position 6.

Example 5: Preparation of 6S- and 6R-3'-Aza-2'-[$^{18}$F]Fluoro-5-MTHF (6S- and 6R-[$^{18}$F]1)$^a$

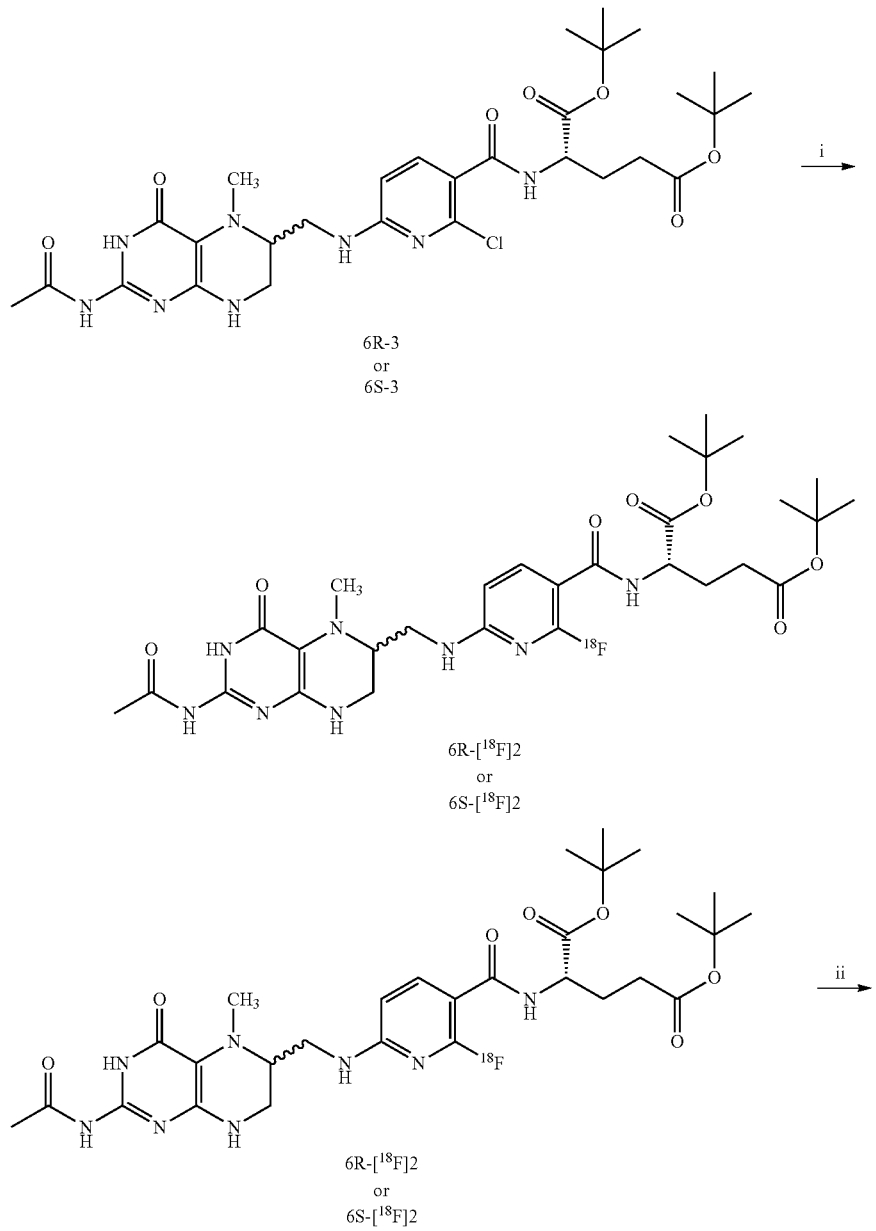

-continued

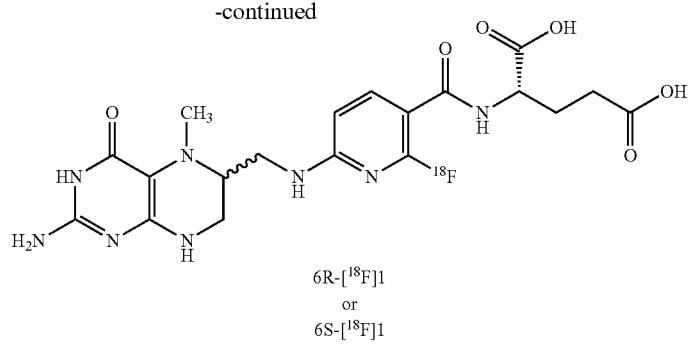

6R-[$^{18}$F]1
or
6S-[$^{18}$F]1

$^{a}$ (i) [$^{18}$F]CsF-K$_{2.2.2}$, DMSO, 160° C., 10 min; (ii) 4M HCl, 70° C., 10 min.

Radiosyntheses of 6S- and 6R-3'-aza-2'-[$^{18}$F]fluoro-5-MTHF were performed in analogy to the radiosynthesis of 3'-aza-2'-[$^{18}$F]fluorofolic acid previously described in literature (Betzel et al, (2013) Radiosynthesis and Preclinical Evaluation of 3'-Aza-2-[18F]fluorofolic Acid: A Novel PET Radiotracer for Folate Receptor Targeting. Bioconjug. Chem. 24, 205-214.) The precursor 6R- or 6S-N$^2$-acetyl-3'-aza-2'-chloro-5-MTHF di-tert-butylester (6R- or 6S-2, 2.50 mg, 3.85 μmol) was dissolved in anhydrous DMSO (300 μL) and added to the azeotropically dried [$^{18}$F]fluoride-cryptate complex (30-35 GBq). The reaction mixture was heated at 160° C. for 10 min. Then, the solution was allowed to cool down for 5 mM and H$_2$O (5 mL) was added. The solution was passed through a Sep-Pak Plus tC18 cartridge (Waters, preconditioned with 5 mL of MeOH, followed by 10 mL of H$_2$O) for trapping the intermediate 6R- or 6S-[$^{18}$F]2. Unreacted [$^{18}$F]fluoride was removed by rinsing the cartridge with H$_2$O (8 mL). The labeled intermediate 6R- or 6S-[$^{18}$F]2 was eluted by passing MeCN (2.5 mL) through the cartridge into another sealed Wheaton reactor (5 mL). Evaporation of MeCN to near dryness was performed under reduced pressure and a nitrogen stream at 90° C. Cleavage of the protecting groups was carried out by adding 4M HCl solution (1.25 mL) to the reactivial and heating for 10 mM at 70° C. to afford 6R- or 6S-[$^{18}$F]1. The reaction mixture was allowed to cool down for 2 min and 10 mM sodium phosphate buffer pH 7.4 containing 50 mg/mL of Na-(+)-L-ascorbate (2.5 mL) and 4M NaOH (1.0 mL) were added for stabilizing the product and for neutralizing the acidic solution, respectively. Purification of the product was achieved by semipreparative radio-HPLC. The product fraction was collected and passed through a steril filter into a sterile and pyrogen-free vial. Quality control of 6R- or 6S-[$^{18}$F]1 was performed on an analytical radio-HPLC. At the end of synthesis, 350-1600 MBq (1-5% d.c. yield) of the final radiotracers were obtained. SA ranged from 46-250 GBq/μmol and radiochemical purity was greater 95%.

Semipreparative radio-HPLC purification was performed using 0.1% EtOH in 10 mM NaH$_2$PO$_4$/Na$_2$HPO$_4$ (pH 7.4) and 50 mg/mL of Na-(+)-L-ascorbate (solvent A) and 40% EtOH in 10 mM NaH$_2$PO$_4$/Na$_2$HPO$_4$ (pH 7.4) and 50 mg/mL of Na-(+)-L-ascorbate (solvent B) as a solvent system with a gradient from 0-15 min 100-85% A, 15-40 min 85% A, and a flow rate of 4 mL/min (280 nm). Analytical radio-HPLC was performed using 50 mM NaH$_2$PO$_4$ (pH 6.5) (solvent A) and 30% MeCN in 50 mM NaH$_2$PO$_4$ (pH 8.0) (solvent B) as a solvent system with a gradient from 0-14-100-45% A, 14-17 min 45-0% A, 17-25 min 0% A, 25-26 min: 0-100% A, 26-32 min: 100% A, and a flow rate of 1 mL/min (280 nm).

Example 6: Determination of Distribution Coefficient

The distribution coefficient (log D$_{7.4}$) of 6S-[$^{18}$F]1 and 6R-[$^{18}$F]1 were determined using the shake flask method reported in literature (Table 1) (Boss et al, (2015) Comparative Studies of Three Pairs of α- and γ-Conjugated Folic Acid Derivatives Labeled with Fluorine-18. Bioconjug. Chem. acs.bioconjchem.5b00644; Wilsonet al, (2001) An admonition when measuring the lipophilicity of radiotracers using counting techniques. Appl. Radiat. Isot. 54, 203-208.) Briefly, the radiotracer was added to a mixture of phosphate buffer (500 μL, pH 7.4) and n-octanol (500 μL) at room temperature. The samples were shaken for 15 min in an overhead shaker and centrifuged for 3 min at 5000 rpm to separate the two phases. Aliquots (50 μL) of both phases were added to Eppendorftubes and then, analyzed in a γ-counter (Wizard, PerkinElmer). The partition coefficient is expressed as the radio between the radioactivity concentrations (cpm/mL) of the n-octanol and the phosphate buffer phase. Values represent the mean±standard deviation of sextuples from two independent experiments.

TABLE 1

Overview of the LogD$_{7.4}$ values of the folates and pteroates.

| Compound | logD$_{7.4}$ |
| --- | --- |
| 6S-[$^{18}$F]1 | −4.6 ± 0.1 |
| 6R-[$^{18}$F]1 | −4.6 ± 0.1 |

Example 7: In Vitro Characterization

The binding affinities of the non-radioactive reference compounds 6R-1 and 6S-1 were determined using KB cells in a displacement assay with [$^3$H]folic acid. The results (Table 2) showed that the two reference diastereoisomers 6R-1 and 6S-1 have similar high affinities to the FR-α and are similar to the values of 6S- and 6R-5-MTHFs. The IC$_{50}$ value for folic acid under the same experimental conditions was found to be 0.6±0.1 nM, whereas 3'-aza-2'-[$^{18}$F]fluorofolic acid exhibited an IC$_{50}$ value of 1.4±0.5 nM. Compared to the oxidized form, the corresponding reduced aza-folate derivatives, 6R-1 and 6S-1, show about 17-fold lower affinity to the FR-α.

TABLE 2

Comparison of in vitro binding affinity data of 6R- and 6S-3'-aza-2'-fluoro-5-MTHF (6R-1 and 6S-1) in comparison to 6R- and 6S-5-MTHF and folic acid to the FR-α. (n = 3).

| Compound | IC$_{50}$ [nM] |
|---|---|
| Folic Acid | 0.6 ± 0.1 |
| 6S-5-MTHF | 20.6 ± 0.4 |
| 6R-5-MTHF | 25.8 ± 5.8 |
| 6S-1 | 23.8 ± 4.0 |
| 6R-1 | 27.1 ± 3.7 |

Example 8: Cell Uptake and Internalization

Figure 22:
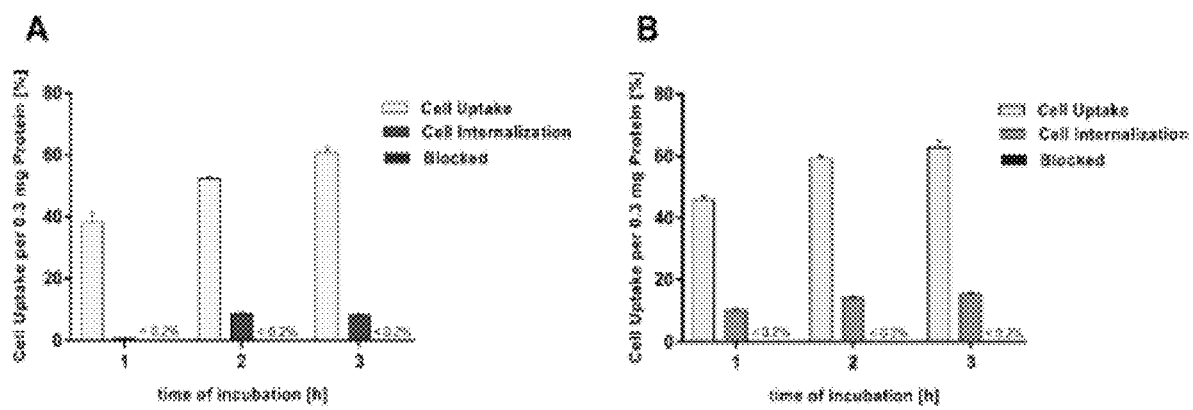
FIG. 22: Uptake and internalization of 6R-($^{18}$9)1 (A) or 6S-[$^{18}$F]1(B) with FR-positive KB cells incubating at 37° C. for 1, 2, or 3 h. Blocking studies were performed using an excess of folic acid.

In order to investigate FR-specific cell uptake and internalization, cell uptake and internalization of 6R-[$^{18}$F]1 and 6S-[$^{18}$F]1 were carried out using FR-positive KB cells. Cell uptake increased constantly over time for both diastereoisomers resulting in an uptake of about 60% (calculated per 0.3 mg of protein) of total added radioactivity after 3 h of incubation at 37° C. (FIG. 22). The internalized activity was found to be around 8% for 6R-[$^{18}$F]1 and about two-fold higher for 6S-[$^{18}$F]1 (16%). 6R-[$^{18}$F]1 and 6S-[$^{18}$F]1 showed high in vivo stability. Only intact parent compounds were found in samples taken 30 min p.i. of the radiotracers. 6R- and 6S-[$^{18}$F]1 were even more stable than the oxidized folic acid tracer, where radiometabolites in the liver were detected. Blocking of FR-α by co-incubating the radiotracers with an excess of folic acid resulted in inhibition of radiofolate uptake to less than 0.2%.

Example 9: Metabolite Studies

Figure 4:
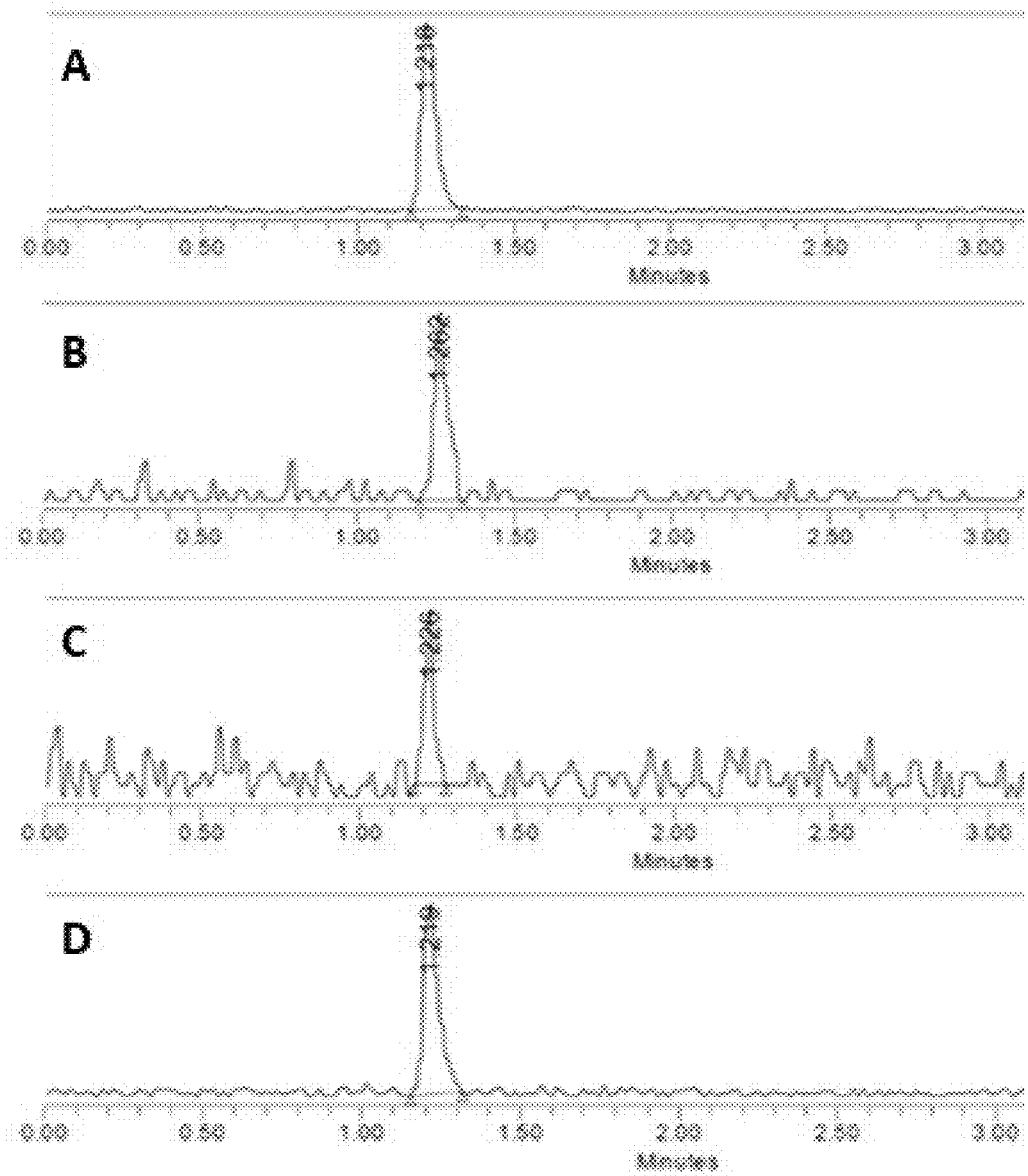
FIG. 4: Radio-UPLC chromatograms of reference radiotracer 6S/6R-[$^{18}$F]1 (A), liver sample (B), blood plasma (C) and urine sample (D) 60 min after injection of 6S/6R-[$^{18}$F]1. Retention time is indicated above the peak.

The folate radiotracer 6S/6R-[$^{18}$F]5 (1:1 ratio, 53.7-52.3 MBq; 0.62-1.15 nmol) were intravenously injected into mice in order to determine the in vivo stability of the tracers. Mice were sacrificed 60 min post injection of the tracer and blood, urine and liver were collected and analyzed. Ice-cold methanol containing 10 mg/mL 2-mercaptoethanol and 0.025% (v/v) ammonium hydroxide was added to the blood plasma, homogenized liver and urine in order to precipitate the proteins.[6] After centrifugation, the supernatants of the blood plasma, liver and urine samples were analyzed by radio-UPLC (FIG. 4). The analysis of the samples revealed only intact parent tracer 6S/6R-[$^{18}$F]1 60 min after radiotracer injection.

Example 10: In Vivo Investigations of $^{18}$F-Based Reduced Folates: 6R-3'-aza-2'-[$^{18}$F]fluoro-5-MTHF (6R-[$^{18}$F]1) and 6R-3'-aza-2'-[$^{18}$F]fluoro-5-MTHF (6S-[$^{18}$F]1)

Biodistribution studies were performed with 15 KB tumor-bearing mice after injection of 6R-3'-aza-2'-[$^{18}$F]fluoro-5-MTHF (6R-[$^{18}$F]1) resp. 6S-3'-aza-2'-[$^{18}$F]fluoro-5-MTHF (6S-[$^{18}$F]1). The values for three time points (30 min, 60 min and 90 min after injection of the radiotracer) are given in Table 1 and Table 2. For blocking experiments, mice received 100 μg of folic acid 10 min prior to the tracer and were sacrificed 60 min p.i.

TABLE 1

Biodistribution of 6R-3'-aza-2'-[$^{18}$F]fluoro-5-MTHF (6R-[$^{18}$F]1) in KB tumor-bearing mice at different time points after injection.

| | 6R-3'-aza-2'-[$^{18}$F]fluoro-5-MTHF (6R[$^{18}$F]1) [% IA/g] | | | |
|---|---|---|---|---|
| | 30 min p.i. n = 4 | 60 min p.i. n = 4 | 90 min p.i. n = 4 | 60 min p.i. & Folic Acid n = 3 |
| Blood | 3.13 ± 0.31 | 2.16 ± 0.25 | 1.92 ± 0.19 | 1.52 ± 0.43 |
| Heart | 2.75 ± 0.33 | 2.38 ± 0.18 | 2.39 ± 0.47 | 1.60 ± 0.46 |
| Lung | 3.37 ± 0.32 | 2.80 ± 0.29 | 2.92 ± 0.53 | 1.73 ± 0.43 |
| Spleen | 8.25 ± 0.96 | 8.25 ± 0.88 | 13.0 ± 4.14 | 3.89 ± 0.40 |
| Liver | 14.3 ± 1.36 | 14.1 ± 0.80 | 16.8 ± 3.58 | 9.64 ± 1.55 |
| Gall Bladder | 37.5 ± 11.7 | 39.0 ± 22.17 | 56.7 ± 13.2 | 26.5 ± 16.6 |
| Kidneys | 34.5 ± 2.45 | 27.3 ± 3.07 | 29.8 ± 7.46 | 4.80 ± 1.94 |
| Stomach | 2.20 ± 0.23 | 2.35 ± 0.49 | 2.51 ± 0.42 | 2.02 ± 0.52 |
| Intestines | 7.68 ± 1.28 | 6.93 ± 1.06 | 8.01 ± 2.72 | 5.23 ± 0.73 |
| Feaces | 12.2 ± 3.54 | 17.8 ± 5.09 | 13.1 ± 6.07 | 15.2 ± 1.75 |
| Salivary glands | 7.16 ± 0.51 | 6.49 ± 0.93 | 7.31 ± 1.17 | 2.61 ± 0.70 |
| Muscle | 1.54 ± 0.13 | 1.36 ± 0.15 | 1.48 ± 0.31 | 1.05 ± 0.42 |
| Bone | 2.73 ± 0.14 | 2.43 ± 0.10 | 3.53 ± 0.90 | 1.51 ± 0.34 |
| KB Tumor | 13.3 ± 1.80 | 18.1 ± 2.86 | 23.9 ± 2.74 | 3.41 ± 0.88 |
| Tu-to-blood | 4.27 ± 0.61 | 8.47 ± 1.62 | 12.5 ± 1.46 | |
| Tu-to-liver | 0.94 ± 0.14 | 1.29 ± 0.18 | 1.46 ± 0.26 | |
| Tu-to-kidney | 0.39 ± 0.05 | 0.67 ± 0.14 | 0.83 ± 0.17 | | values shown represent the mean ± S.D. of data from three to four animals

TABLE 2

Biodistribution of 6S-3'-aza-2'-[$^{18}$F]fluoro-5-MTHF (6S-[$^{18}$F]1) in KB tumor-bearing mice at different time points after injection.

| | 6S-3'-aza-2-[$^{18}$F]fluoro-5-MTHF (6S-[$^{18}$F]1) [% IA/g] | | | |
|---|---|---|---|---|
| | 30 min p.i. n = 4 | 60 min p.i. n = 4 | 90 min p.i. n = 4 | 60 min p.i. & Folic Acid n = 3 |
| Blood | 1.52 ± 0.31 | 1.26 ± 0.08 | 1.16 ± 0.20 | 1.09 ± 0.28 |
| Heart | 2.02 ± 0.22 | 1.53 ± 0.15 | 1.48 ± 0.17 | 0.50 ± 0.13 |
| Lung | 2.31 ± 0.42 | 2.04 ± 0.09 | 2.08 ± 0.35 | 0.84 ± 0.20 |
| Spleen | 1.90 ± 0.34 | 1.57 ± 0.16 | 1.82 ± 0.49 | 0.90 ± 0.24 |
| Liver | 8.10 ± 1.16 | 6.28 ± 0.66 | 5.86 ± 1.11 | 4.76 ± 0.87 |
| Gall Bladder | 20.0 ± 9.00 | 16.6 ± 8.91 | 11.4 ± 7.18 | 5.87 ± 0.45 |
| Kidneys | 42.5 ± 2.73 | 37.5 ± 3.61 | 42.3 ± 7.05 | 2.28 ± 0.95 |
| Stomach | 2.54 ± 0.56 | 1.84 ± 0.33 | 1.69 ± 0.33 | 0.73 ± 0.32 |
| Intestines | 2.61 ± 0.65 | 2.58 ± 0.42 | 2.34 ± 0.39 | 4.34 ± 0.93 |
| Feaces | 3.71 ± 2.34 | 4.85 ± 1.95 | 4.57 ± 1.98 | 8.42 ± 2.10 |
| Salivary glands | 13.8 ± 2.06 | 13.8 ± 1.28 | 21.4 ± 4.59 | 0.89 ± 0.26 |
| Muscle | 1.36 ± 0.25 | 1.29 ± 0.14 | 1.24 ± 0.14 | 0.26 ± 0.06 |
| Bone | 1.70 ± 0.13 | 1.38 ± 0.14 | 1.49 ± 0.30 | 0.49 ± 0.12 |
| KB Tumor | 11.1 ± 0.90 | 14.2 ± 1.91 | 19.2 ± 4.16 | 2.11 ± 0.38 |
| Tu-to-blood | 7.41 ± 0.96 | 11.3 ± 1.13 | 16.5 ± 0.59 | |
| Tu-to-liver | 1.38 ± 0.16 | 1.87 ± 0.96 | 3.30 ± 0.59 | |
| Tu-to-kidney | 0.26 ± 0.01 | 0.38 ± 0.04 | 0.45 ± 0.07 | | values shown represent the mean ± S.D. of data from three to four animals.

Figure 5:
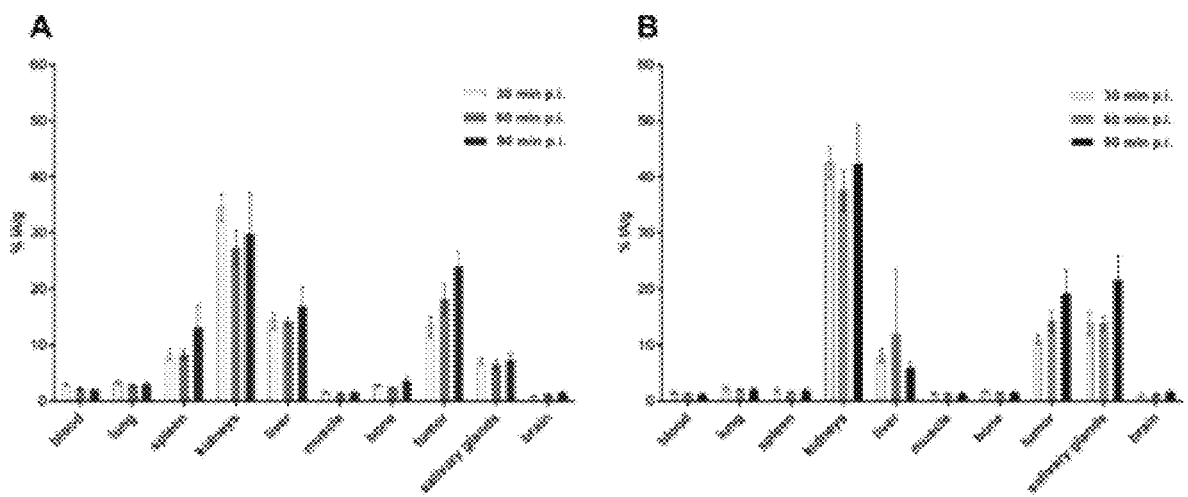
FIG. 5: Radioactivity accumulation of 6R-3'-aza-2'-[$^{18}$F]fluoro-5-MTHF (A) and 6S-3'-aza-2'-[$^{18}$F]fluoro-5-MTHF (B) in some selected tissues at 30, 60 and 90 min p.i.

Biodistribution studies revealed high tumor uptake for both 6R- and 6S-diastereoisomers. At already 30 min p.i., a high tumor uptake of 13.3±1.80% IA/g for 6R-[$^{18}$F]1 and 11.13±0.90% IA/g for 6S-[$^{18}$F]1 was observed (FIG. 5). Tumor uptake further increased over time to 23.9±2.74% IA/g for the 6R-isomer and to 19.2±4.16% IA/g for the 6S-isomer at 90 min p.i. This value is approximately twice the amount of radioactivity accumulation obtained from the oxidized tracer 3'-aza-2'-[$^{18}$F]fluorofolic acid (12.59±1.77% IA/g). Tumor uptake was efficiently blocked by pre-injection of folic acid. Specificity of tumor binding was 85% and 89% for the R- and 6S-isomers, respectively. A significant higher amount of radioactivity was found in the liver for the 6R-tracer (14.3±1.36% IA/g) compared to the 6S-tracer (8.10±1.16% IA/g) 30 min p.i. At 90 min p.i., radioactivity uptake in the liver slightly increased for the 6R-isomer (16.8±3.58% IA/g), whereas radioactivity levels decreased for the S-isomer (5.86±1.11% IA/g). Spleen uptake noticeably increased for the 6R-isomer already at 30 min p.i. and at 90 min p.i. a seven-fold higher uptake was observed for the 6R-isomer (13.0±4.14% IA/g) compared to the 6S-isomer (1.82±0.49% IA/g). In contrast, kidney uptake was considerably higher for 6S-[$^{18}$F]1 compared to the 6R-[$^{18}$F]1 at 30 min p.i. (6R-form: 34.5±2.45% IA/g, 6S-form: 42.5±2.73% IA/g) and remained nearly constant over time for both diastereoisomers (90 min p.i.: 6R-form: 29.8±7.46% IA/g, 6S-form: 42.3±7.05% IA/g). However, both values were considerably lower compared to 3'-aza-2'-[$^{18}$F]fluorofolic acid (57.3±8.40% IA/g). A significant difference in salivary glands uptake was also observed for the two diastereoisomers, where a three-fold higher amount of 6S-isomer was found in the salivary glands 90 min p.i. (6R-form: 7.31±1.17% IA/g, 6S-form: 21.4±4.59% IA/g).

Figure 6:
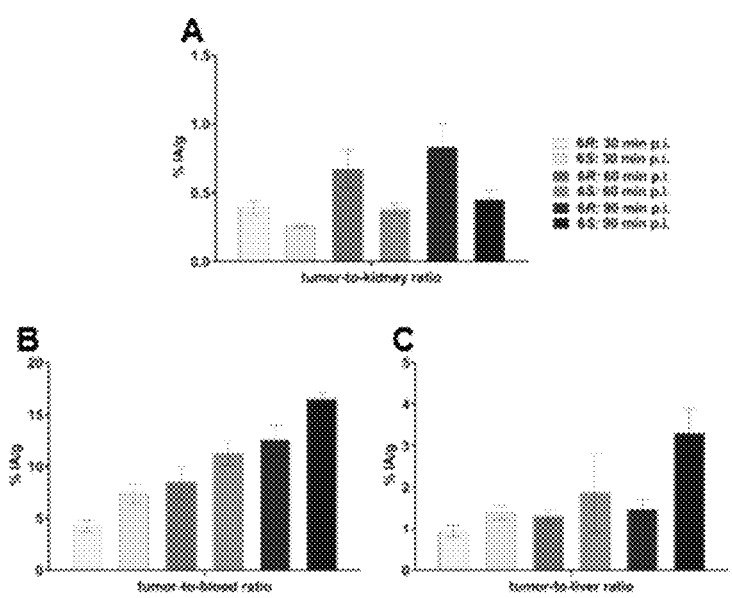
FIG. 6: Comparison of the tumor-to-kidney (A), tumor-to-blood (B) and tumor-to-liver (C) ratios of 6R-[$^{18}$F]1 and 6S-[$^{18}$F]1.

Tumor-to-kidney ratio was significantly lower for 6S-[$^{18}$F]1 (30 min p.i.: 0.26±0.01% IA/g) and increased by a factor of 1.7 to a value of 0.45±0.07% IA/g at 90 min p.i. (FIG. 6). In contrast, the tumor-to-kidney ratio of 6R-[$^{18}$F]1 was already 0.39±0.05% IA/g at 30 min p.i. and increased by a factor of 2.1 to 0.83±0.17% IA/g at 90 min p.i. Tumor-to-kidney ratio of 6R-[$^{18}$F]1 therefore is approximately two- and four-fold higher compared to 6S-[$^{18}$F]1 and 3'-aza-2'-[$^{18}$F]fluorofolic acid, respectively. Tumor-to-liver ratio was higher for the 6S-isomer compared to the 6R-isomer at all investigated time points due to the lower liver uptake of 6S-[$^{18}$F]1. So at 90 min p.i. in the liver, a three-fold higher accumulation of 6R-[$^{18}$F]1 compared to the 6S-isomer (6R-form: 16.8±3.58% IA/g, 6S-form: 5.86±1.11% IA/g) was observed. The lower uptake of the S-isomer in the liver is advantageous from an imaging point of view as it would permit delineating FR-positive tumors that are located close to the liver. The tumor-to-blood ratios increased constantly over time for both isomers, whereby the ratios of the 6S-isomer were significantly higher compared to the 6R-isomer.

Figure 7:
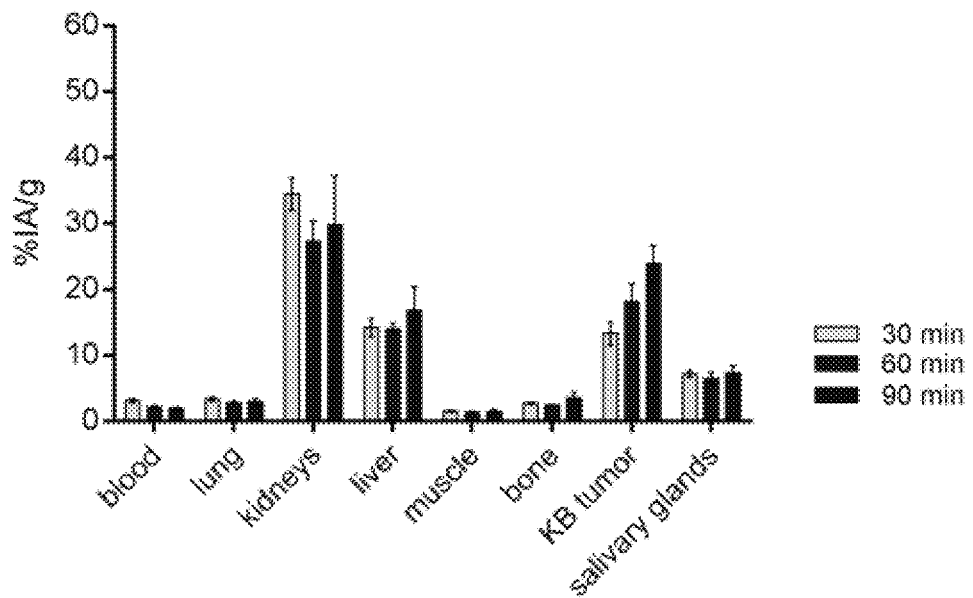
FIG. 7: Tissue distribution profile at 30, 60 and 90 min after injection of $^{18}$F-6R-5Me-AzaTHF.
Figure 8:
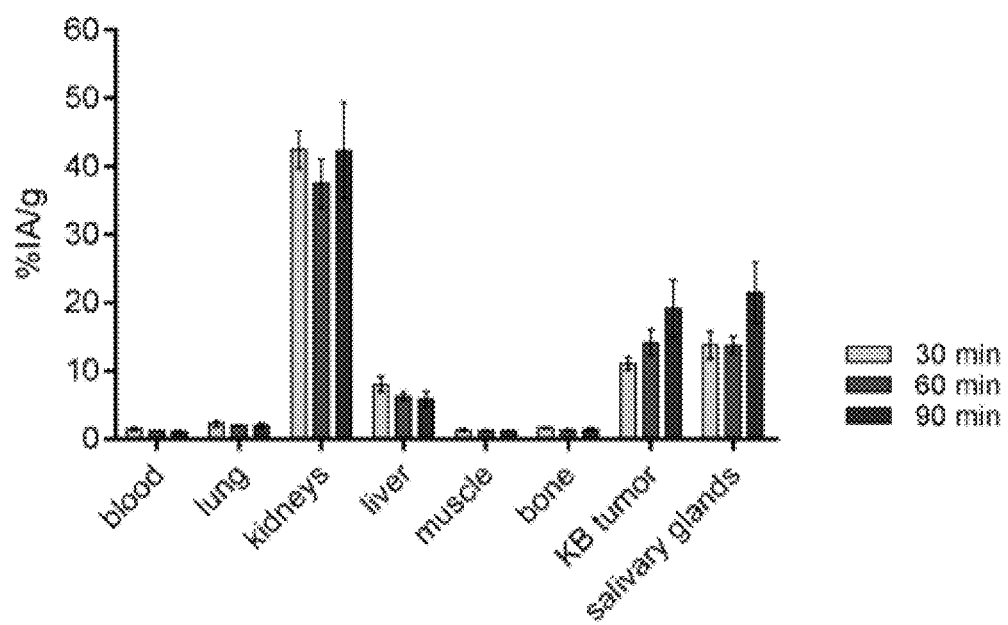
FIG. 8: Tissue distribution profile at 30, 60 and 90 min after injection of $^{18}$F-6S-5Me-AzaTHF.

The time-dependent tissue distribution of the in the most relevant organs and tissues are shown in FIGS. 7 and 8.

Figure 9:
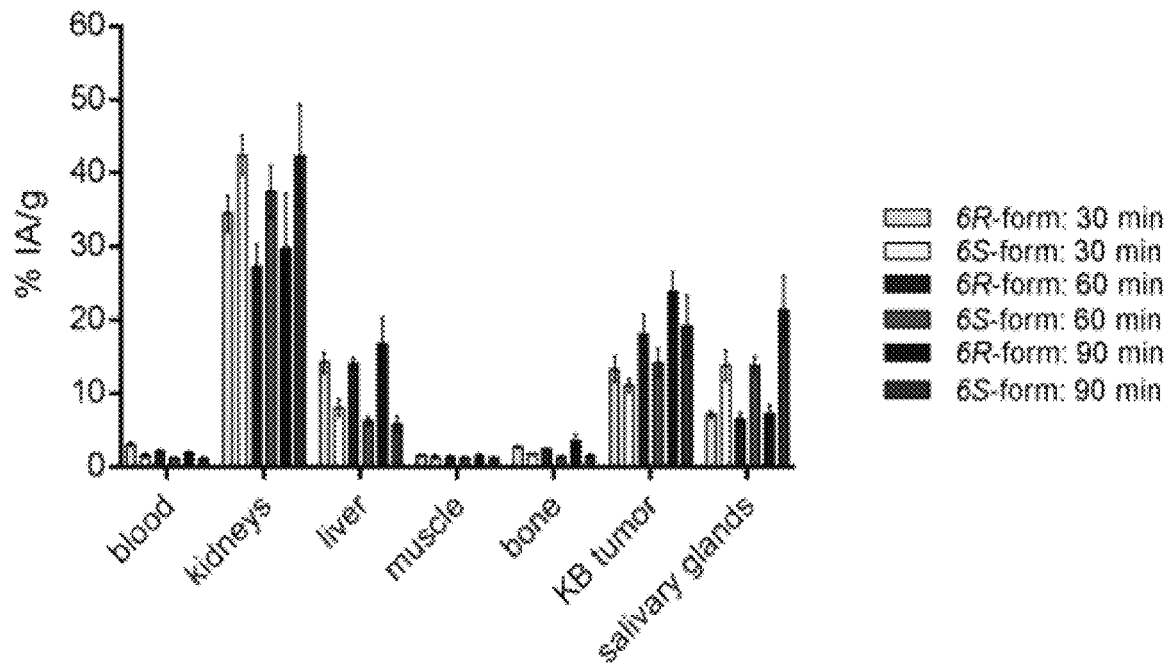
FIG. 9: Comparison of the tissue distribution profile of $^{18}$F-6R-5Me-AzaTHF (6R-form) and the $^{18}$F-6S-5Me-AzaTHF (6S-form).

The accumulated activity of two $^{18}$F-folate tracers in different organs and tissues is shown in FIG. 9.

Figure 10:
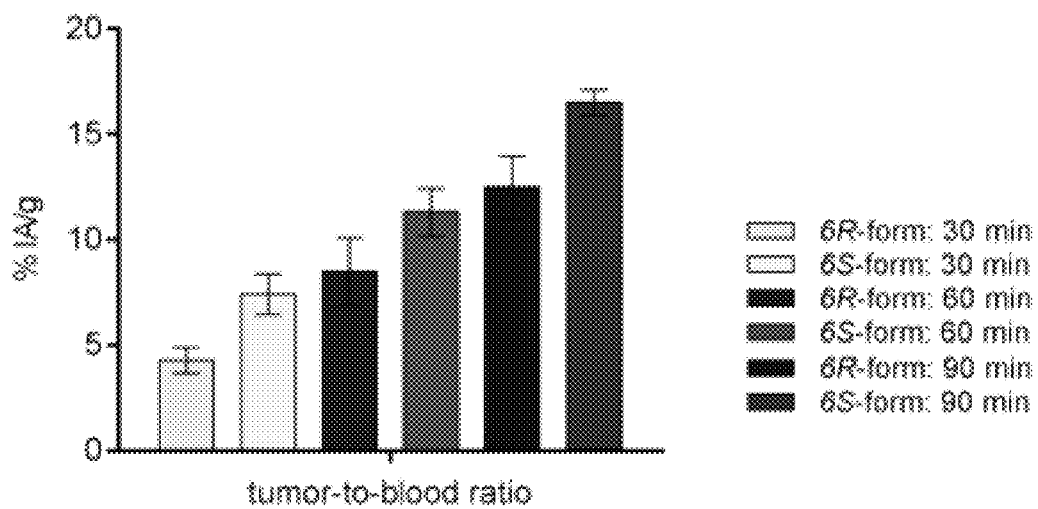
FIG. 10: Comparison of the tumor-to-blood ratios of $^{18}$F-6R-5Me-AzaTHF (6R-form) and the $^{18}$F-6S-5Me-AzaTHF (6S-form).
Figure 11:
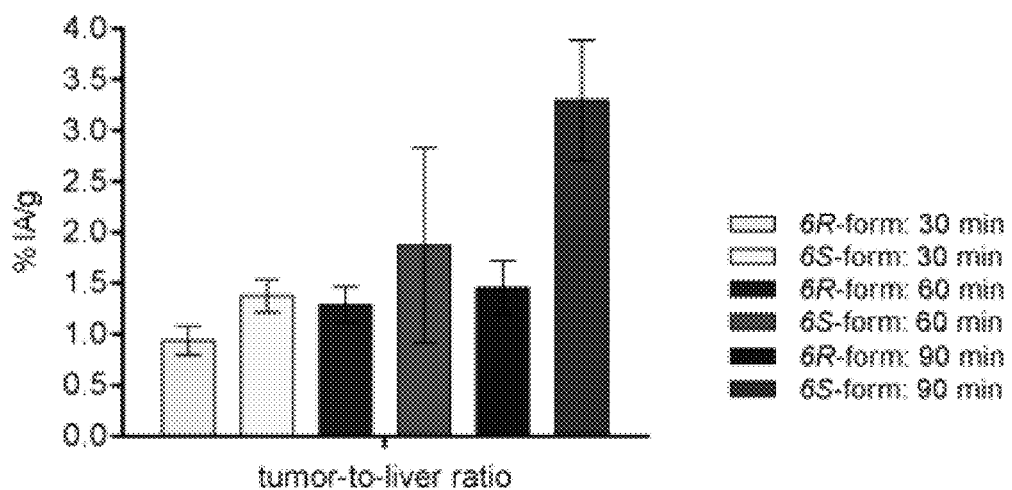
FIG. 11: Comparison of the tumor-to-liver ratios of $^{18}$F-6R-5Me-AzaTHF (6R-form) and the $^{18}$F-6S-5Me-AzaTHF (6S-form).
Figure 12:
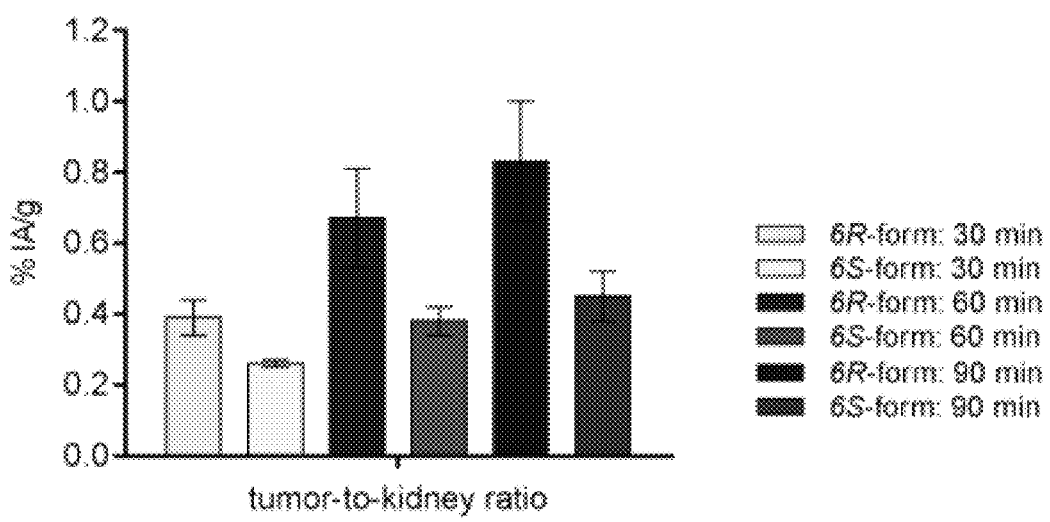
FIG. 12: Comparison of the tumor-to-kidney ratios of $^{18}$F-6R-5Me-AzaTHF (6R-form) and the $^{18}$F-6S-5Me-AzaTHF (6S-form).
Figure 13:
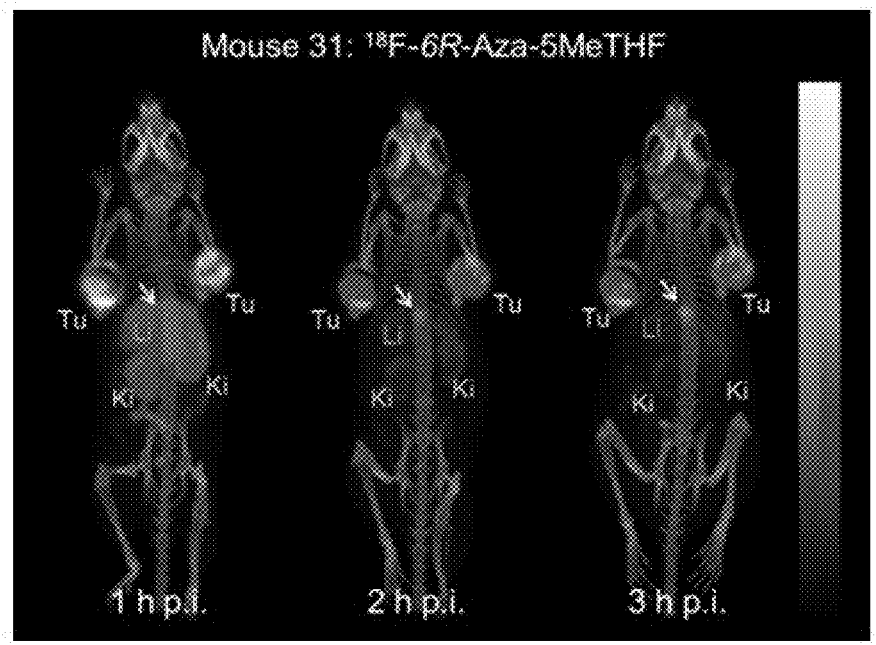
FIG. 13: PET/CT scans of a KB tumor-bearing mouse 1 h, 2 h and 3 h after injection of $^{18}$F-6R-Aza-5MeTHF. (Tu=tumor xenografts, Li=liver, Ki=kidney, white arrow=gall bladder).
Figure 14:
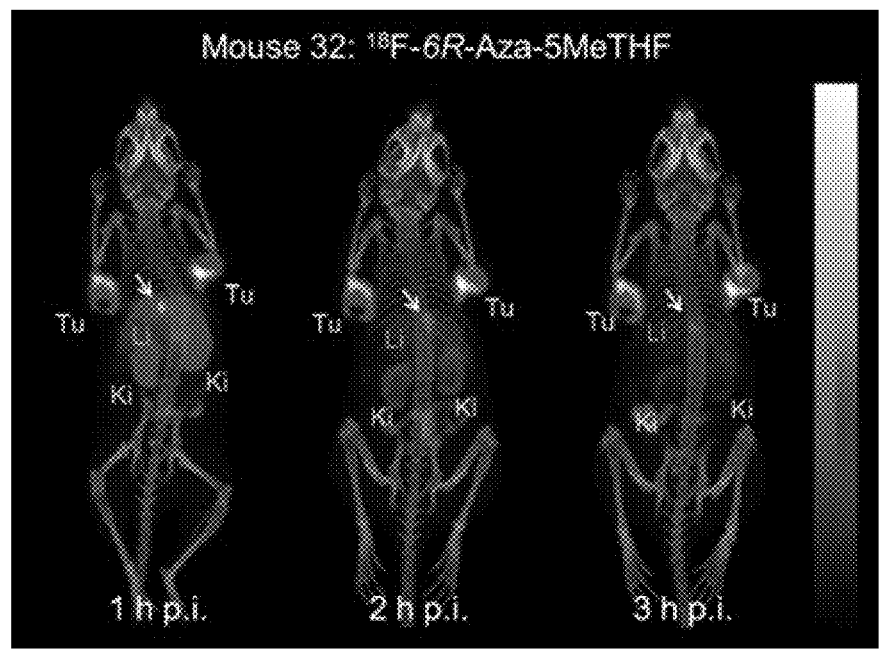
FIG. 14: PET/CT scans of a KB tumor-bearing mouse 1 h, 2 h and 3 h after injection of $^{18}$F-6R-Aza-5MeTHF. (Tu=tumor xenografts, Li=liver, Ki=kidney, white arrow=gall bladder).

Tumor-to-background ratios at 30 min, 60 min and 90 min after injection of each radiotracer are shown in FIG. 10-12.

Example 11: PET/CT Imaging Studies

The experimental plan is given in Table 3.

| Mouse 31 | Mouse 32 | Mouse 33 | Mouse 34 | Mouse 35 | Mouse 36 |
|---|---|---|---|---|---|
| — | — | Folic Acid | — | — | Folic Acid |
| $^{18}$F-6R-Aza-5MeTHF | | | $^{18}$F-6S-Aza-5MeTHF | | |
| Scan: 1 h p.i. | Scan: 1 h p.i. | Scan: 1 h p.i. | Scan: 1 h p.i. | Scan: 1 h p.i. | Scan: 1 h p.i. |
| Scan: 2 h p.i. | Scan: 2 h p.i. | Scan: 2 h p.i. | Scan: 2 h p.i. | Scan: 2 h p.i. | Scan: 2 h p.i. |
| Scan: 3 h p.i. | Scan: 3 h p.i. | Scan: 3 h p.i. | Scan: 3 h p.i. | Scan: 3 h p.i. | Scan: 3 h p.i. |

PET/CT mages (maximal intensity projections (MIPs)) of each mouse scanned at 1 h, 2 h and 3 h after injection of the radiotracer are shown in FIG. 13-18.

Figure 15:
FIG. 15: PET/CT scans of a KB tumor-bearing mouse 1 h, 2 h and 3 h after injection of excess folic acid prior to $^{18}$F-6R-Aza-5MeTHF. (Li=liver, white arrow=gall bladder).
Figure 16:
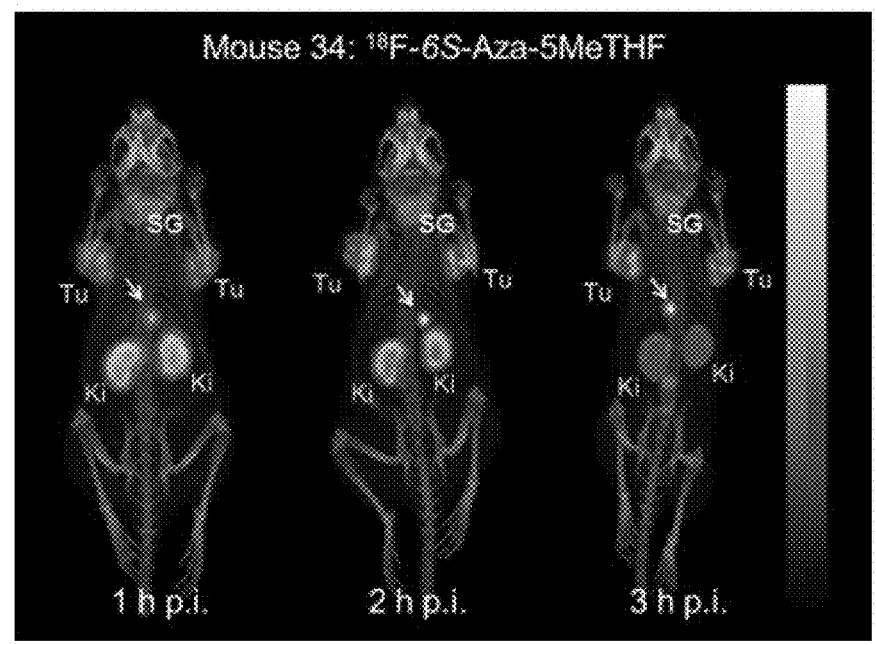
FIG. 16: PET/CT scans of a KB tumor-bearing mouse 1 h, 2 h and 3 h after injection of $^{18}$F-6S-Aza-5MeTHF. (Tu=tumor xenografts, Ki=kidney, SG=salivary glands, white arrow=gall bladder, green arrow=choroid plexus).
Figure 17:
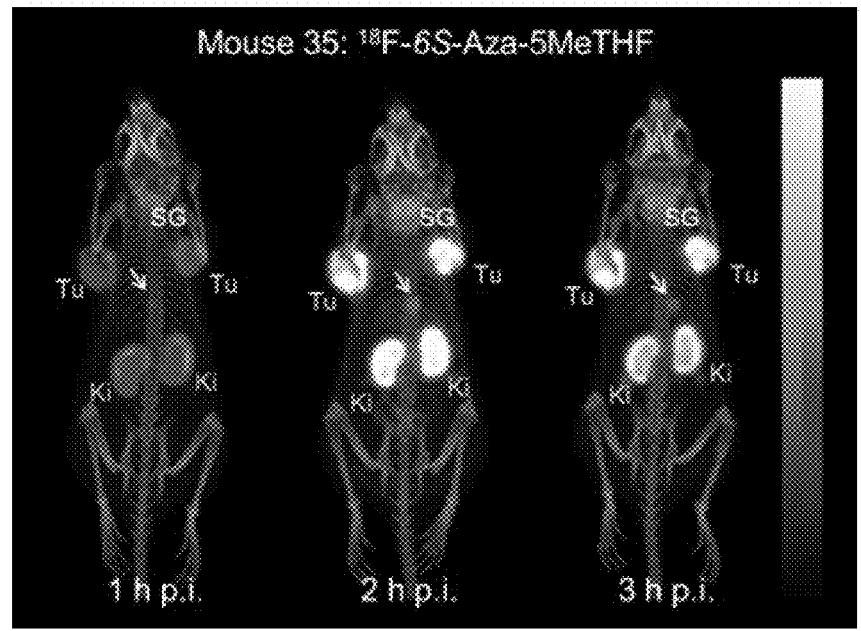
FIG. 17: PET/CT scans of a KB tumor-bearing mouse 1 h, 2 h and 3 h after injection of $^{18}$F-6S-Aza-5MeTHF. (Tu=tumor xenografts, Ki=kidney, SG=salivary glands, white arrow=gall bladder, green arrow=choroid plexus).
Figure 18:
FIG. 18: PET/CT scans of a KB tumor-bearing mouse 1 h, 2 h and 3 h after injection of excess folic acid prior to $^{18}$F-6S-Aza-5MeTHF. (Bl=urinary bladder, white arrow=gall bladder).
Figure 19:
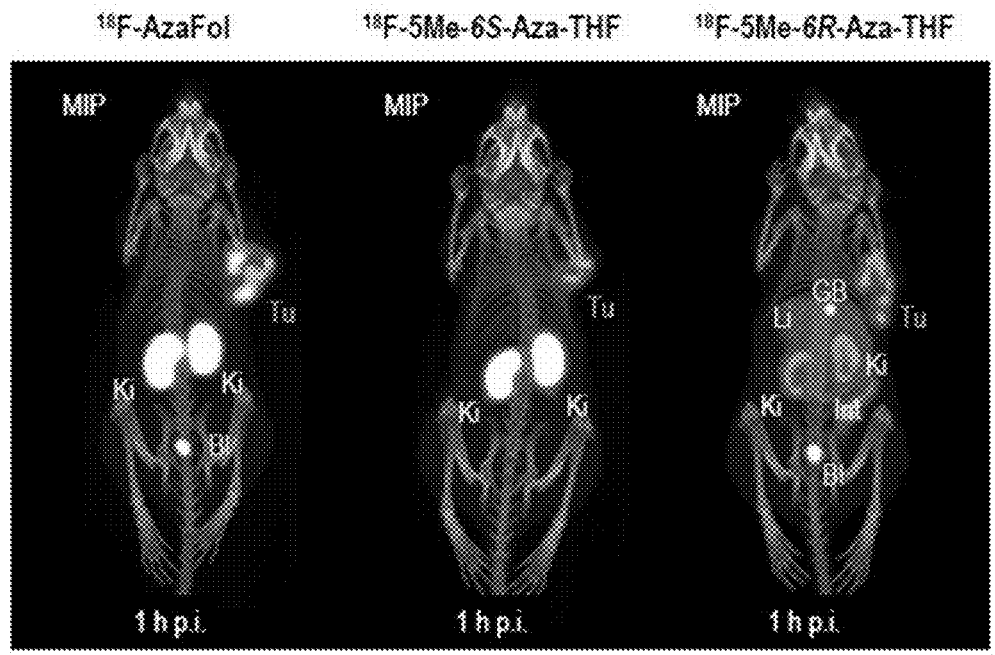
FIG. 19: PET/CT scans of a IGROV-1 (human ovarian carcinoma cell line) tumor-bearing mouse 1 h after injection of 18F-AzaFol, 18F-5Me-6S-Aza-THF and 18F-5Me-6R-Aza-THF (Tu=tumor xenografts, Ki=kidney, SG=salivary glands, white arrow=gall bladder, green arrow=choroid plexus).
Figure 20:
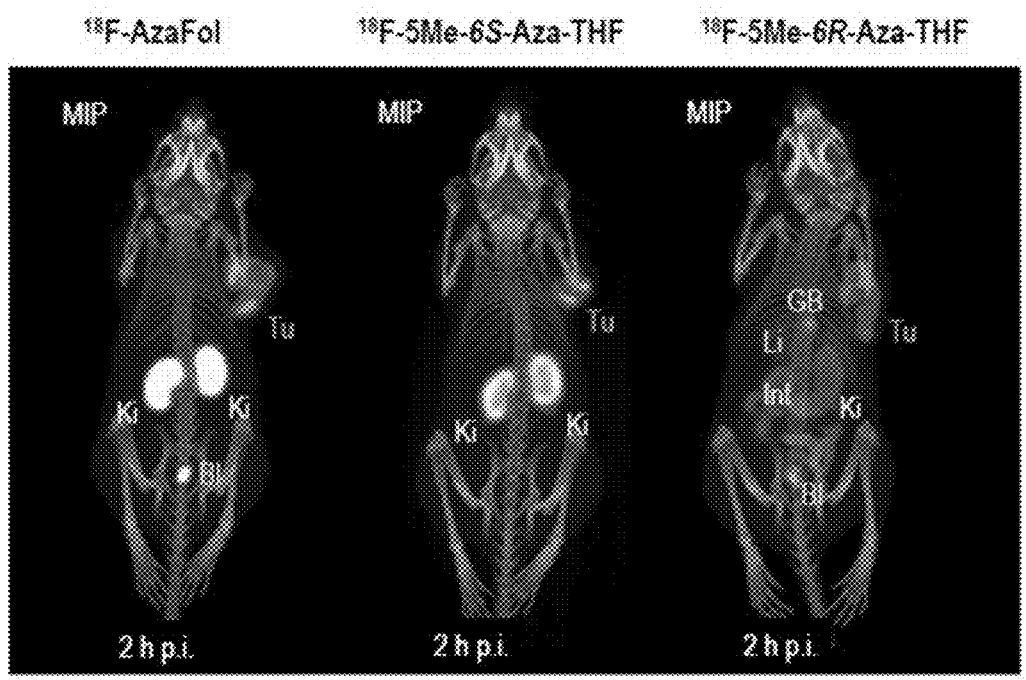
FIG. 20: PET/CT scans of a IGROV-1 (human ovarian carcinoma cell line) tumor-bearing mouse 2 h after injection of 18F-AzaFol, 18F-5Me-6S-Aza-THF and 18F-5Me-6R-Aza-THF (Tu=tumor xenografts, Ki=kidney, SG=salivary glands, white arrow=gall bladder, green arrow=choroid plexus).
Figure 21:
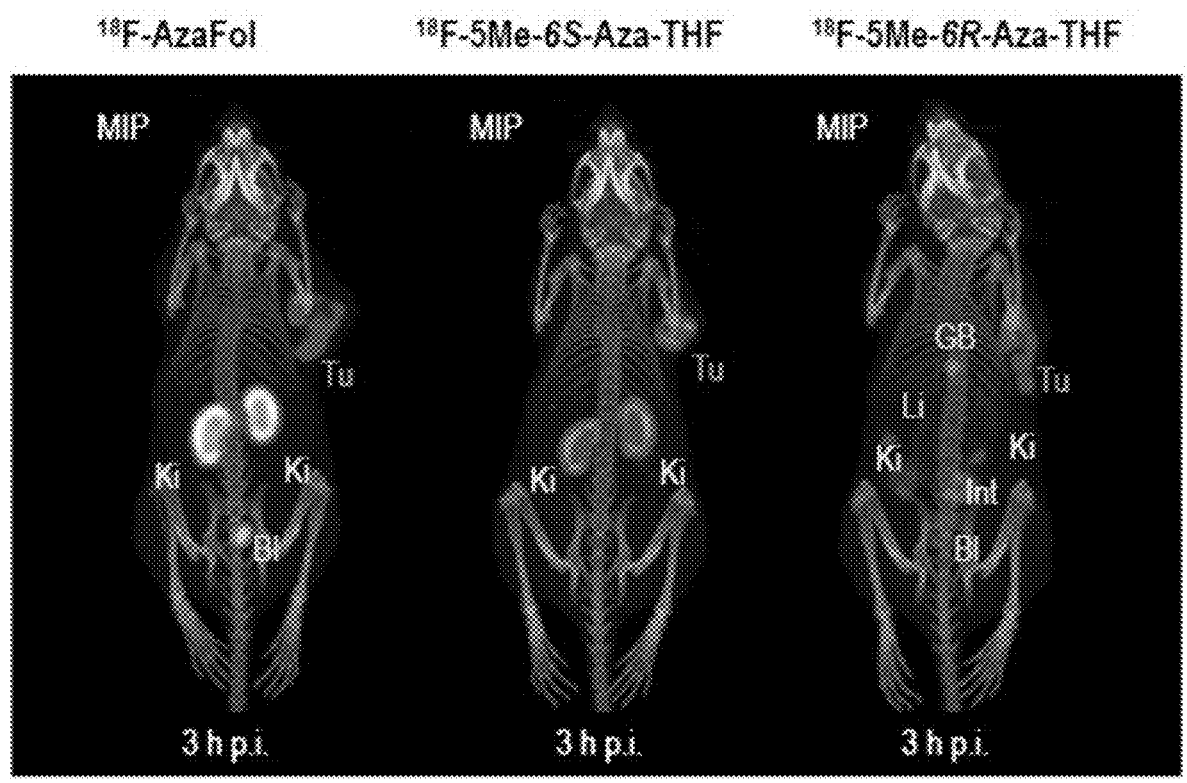
FIG. 21: PET/CT scans of a IGROV-1 (human ovarian carcinoma cell line) tumor-bearing mouse 3 h after injection of 18F-AzaFol, 18F-5Me-6S-Aza-THF and 18F-5Me-6R-Aza-THF (Tu=tumor xenografts, Ki=kidney, SG=salivary glands, white arrow=gall bladder, green arrow=choroid plexus).

High KB tumor xenograft uptake was observed for both radiotracers already 1 h p.i. and the tumors were very well visualized with high intensity at 3 h p.i. for both compounds. Radioactivity accumulation in the liver was mainly observed for the 6R-isomer, however, after 3 h p.i. liver uptake was only barely visible. FR-positive kidneys were clearly visualized 1 h p.i. with 6R-[$^{18}$F]1, but nearly invisible at 3 h p.i. In contrast, high kidney accumulation was observed for 6S-[$^{18}$F]1 at all investigated time points. Furthermore, high radioactivity uptake was evident in the salivary glands. Blocking studies were performed by injecting folic acid 10 minutes prior to the administration of the radiotracers and resulted in a remarkably reduced uptake of 6R-[$^{18}$F]1 and 6S-[$^{18}$F]1 in all FR-positive tissues (KB tumor xenografts, kidneys, salivary glands and choroid plexus) (FIG. 15 and FIG. 17).

Based on the biodistribution and PET imaging results, it can be concluded that the 6S-isomer is excreted preferably via the renal pathway, whereas the 6R-isomer seems to be excreted mainly via the hepatobiliary pathway.

Example 12: Cell Uptake and Internalization Studies were Performed with FR-α and FR-β Transfected CHO Cells Referred to as RT16 and D4 Cells The uptake and internalization of the oxidized ($^{18}$F-AzaFol) and reduced $^{18}$F-folates (6S-isomer and 6R-isomer of $^{18}$F-5-Me-Aza-THF) in D4 and RT16 cells which express the FR-α and FR-β, respectively was studied. Both cell lines were kindly provided by Larry Matherly Wayne State University, Detroit, U.S.; Golani et al., J Med Chem, 2016, 59, 7856.

When using RT16 tumor cells that express the FR-α, all three $^{18}$F-folate tracers (oxidized and reduced versions) showed similar uptake, which ranges between 43-50% after 1 h incubation and 56-66% after 3 h incubation. The internalized fraction of the radiotracers reached 8-10% after 1 h and increased slightly up to 9-12% after 3 h incubation.

When using D4 cells that express the FR-β, the uptake of $^{18}$F-AzaFol and the 6S-isomer of the reduced radiotracer reached approximately 70% after 1 h incubation and 80% after 3 h incubation. The internalized fraction of $^{18}$F-AzaFol and the 6S-isomer of the reduced version was 20% and 12%, respectively, after 1 h incubation. These numbers increased slightly when the incubation time was extended to 3 h. However, using this D4 cells revealed that only 3% of reduced folate radiotracer (6R-isomer) were taken up and about 1% was internalized. No change was observed after additional two hours of incubation.

Figure 23:
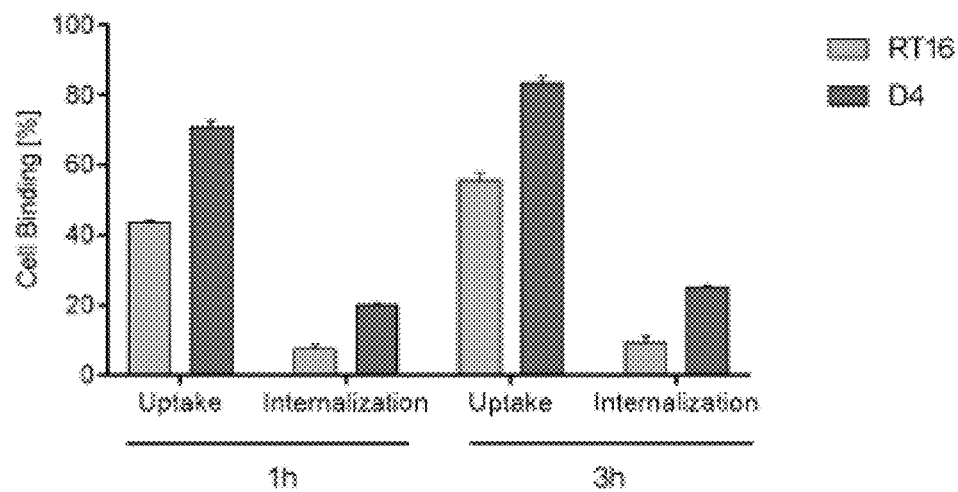
FIG. 23: Total uptake and internalization of 18F-AzaFol, using RT16 (FR-α) and D4 (FR-β) cell lines.
Figure 24:
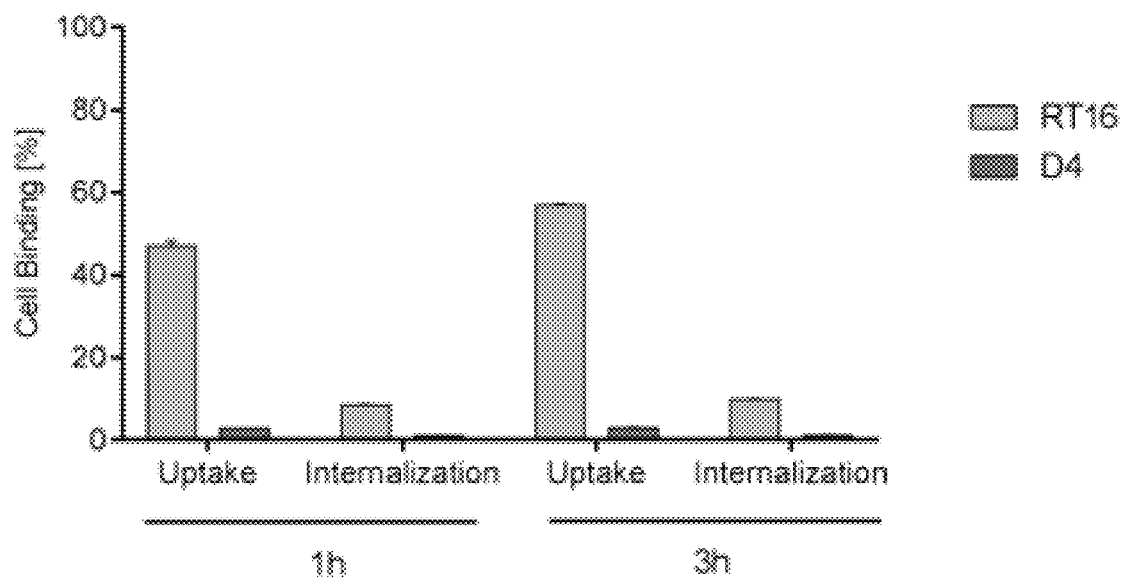
FIG. 24: Total uptake and internalization of 6R-3-aza-2-${}^{18}$F-5-MTHF using RT16 (FR-α) and D4 (FR-β) cell lines.
Figure 25:
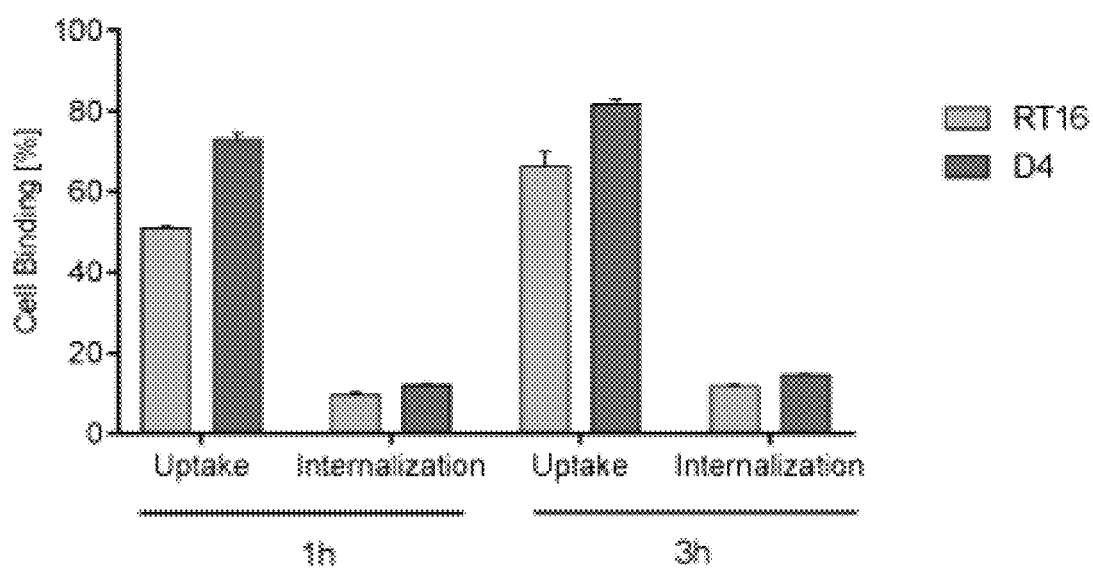
FIG. 25: Total uptake and internalization of 6S-3-aza-2-${}^{18}$F-5-MTHF using RT16 (FR-α) and D4 (FR-β) cell lines.
Figure 26:
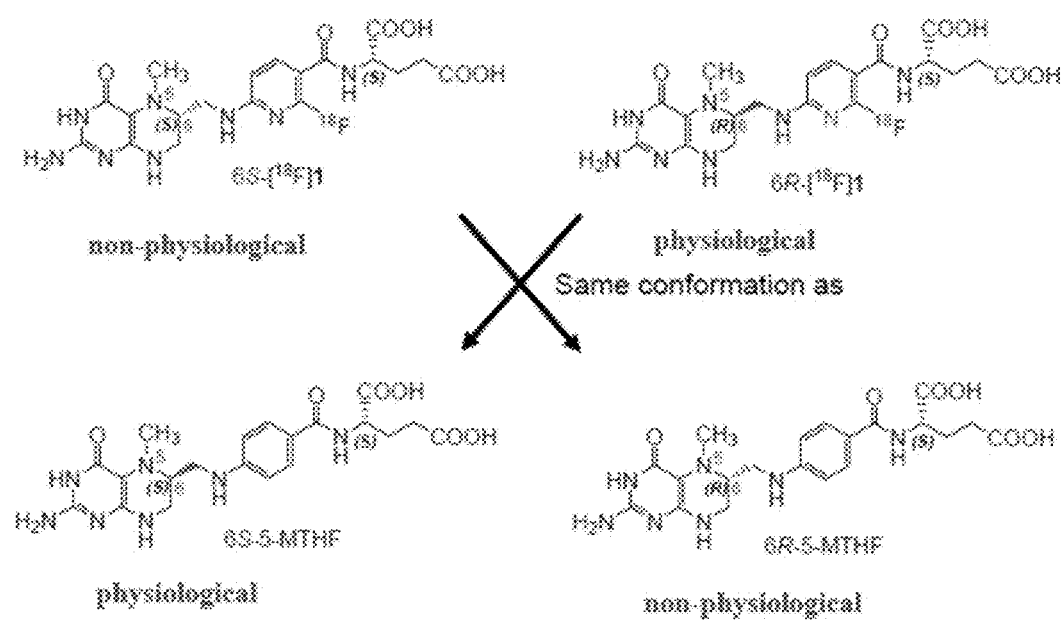
FIG. 26: Structure and stereochemical denomination of reduced ${}^{18}$F-folates and unfluorinated isomers.

A significant uptake of 18F-AzaFol and the reduced version of the radiotracer (6S-isomer) was observed when using RT16 (FR-α) cells as well as when using D4 cells (FR-β) cells (FIG. 23). The 6R-isomer of the reduced folate showed higher uptake into RT16 cells, indicating FR-α-selectivity while uptake into D4 cells was very low (FIG. 24 and FIG. 25). These results were in line with the hypothesis that the 6R-isomer (corresponding to the natural version of reduced folate referred to as 6S-5Me-THF) is selectively binding to the FR-α.

The invention claimed is:

1. A compound of formula Ia or Ib

[Structure Ia]

[Structure Ib]

wherein $R_1$, $R_2$ are independently of each other H or straight chain or branched C1-C6 alkyl, and $R_3$, $R_4$ are independently of each other H, formyl, or methyl, or a pharmaceutically acceptable salt thereof.

2. The compound according to claim 1 wherein $R_1$, $R_2$ are independently of each other H or straight chain or branched C1-C6 alkyl, $R_3$ is methyl, and $R_4$ is H, or a pharmaceutically acceptable salt thereof.

3. The compound of claim 1 according to claim 1 of formulas IIa or IIb

[Structure IIa]

[Structure IIb]

wherein $R_1$, $R_2$ are independently of each other H, or C1-C12 alkyl, or a pharmaceutically acceptable salt thereof.

4. The compound according to claim 1 of formulas IIIa or IIIb

[Structure IIIa]

[Structure IIIb]

or a pharmaceutically acceptable salt thereof.

5. The compound according to claim 1, of a stereoisomeric purity of greater than 99.

6. The compound according to claim 1, wherein the pharmaceutically acceptable salt is an alkali or alkaline earth metal salt.

7. A method for diagnostic imaging of a cell or population of cells expressing a folate-receptor, said method comprising administering at least one compound according to claim 1 in a diagnostic imaging amount, and obtaining a diagnostic image of said cell or population of cells.

8. The method according to claim 7 wherein the diagnostic imaging is performed of a cell or population of cells expressing a folate-receptor in vitro or in vivo.

9. The method according to claim 7 wherein the diagnostic imaging is performed on human ovarian carcinoma cells.

10. A method for in vitro detection of a cell expressing the folate receptor in a tissue sample which includes contacting said tissue sample with a compound according to claim 1 in effective amounts and for sufficient time and conditions to allow binding to occur and detecting such binding.

11. A method of diagnostic imaging or monitoring a subject comprising (i) administering at least one compound according to claim 1 in a diagnostic imaging amount, and (ii) performing diagnostic imaging using PET by detecting a signal from said at least one compound.

12. A method of monitoring cancer or inflammatory and autoimmune disease therapy in a subject comprising (i) administering to a subject in need thereof at least one compound according to claim 1 in a diagnostic imaging amount in combination with a therapeutically active agent for said cancer or autoimmune disease, and (ii) performing diagnostic imaging using PET by detecting a signal from said at least one compound to follow the course of cancer or inflammatory and autoimmune disease therapy.

13. The compound according to claim 1, of a stereoisomeric purity of greater than 99.5%.

14. The compound according to claim 1, wherein the pharmaceutically acceptable salt is a sodium, a potassium, a magnesium or a calcium salt.

15. The method according to claim 10, wherein binding is detected by autoradiography.

* * * * *